(12) United States Patent
Ohta et al.

(10) Patent No.: US 7,518,001 B2
(45) Date of Patent: Apr. 14, 2009

(54) RADICALLY POLYMERIZABLE SULFUR-CONTAINING COMPOUND AND RADICALLY POLYMERIZABLE SULFUR-CONTAINING POLYMER

(75) Inventors: Keisuke Ohta, Oita (JP); Tsuneo Tajima, Oita (JP); Kazufumi Kai, Oita (JP); Yasuyuki Oyama, Oita (JP)

(73) Assignee: Showa Denko K.K., Tokyo (JP)

( * ) Notice: Subject to any disclaimer, the term of this patent is extended or adjusted under 35 U.S.C. 154(b) by 199 days.

(21) Appl. No.: 11/663,228

(22) PCT Filed: Sep. 20, 2005

(86) PCT No.: PCT/JP2005/017658

§ 371 (c)(1),
(2), (4) Date: Mar. 20, 2007

(87) PCT Pub. No.: WO2006/033438

PCT Pub. Date: Mar. 30, 2006

(65) Prior Publication Data

US 2007/0208149 A1 Sep. 6, 2007

Related U.S. Application Data

(60) Provisional application No. 60/613,239, filed on Sep. 28, 2004.

(30) Foreign Application Priority Data

Sep. 21, 2004 (JP) ............................. 2004-273556

(51) Int. Cl.
C07D 327/04 (2006.01)
C08F 290/14 (2006.01)
C08F 299/00 (2006.01)
G08G 75/28 (2006.01)

(52) U.S. Cl. ....................... 549/80; 526/257

(58) Field of Classification Search ................. 526/209, 526/266, 286, 319, 257; 549/80
See application file for complete search history.

(56) References Cited

U.S. PATENT DOCUMENTS

2006/0252900 A1 * 11/2006 Bowman et al. ............ 526/318

FOREIGN PATENT DOCUMENTS

| EP | 0 943 660 A1 | 9/1999 |
|----|----|----|
| JP | 5-247027 A | 9/1993 |
| JP | 8-302013 A | 11/1996 |
| JP | 9-59324 A | 3/1997 |
| JP | 10-67854 A | 3/1998 |
| JP | 11-292969 A | 10/1999 |
| JP | 2004-323702 A | 11/2004 |

OTHER PUBLICATIONS

Wonmun Choi et al., "A Novel Construction of Living Polymerization by Neighboring Group Participation: Living Cationic Ring-Opening Polymerization of a Five-Membered Cyclic Dithiocarbonate", Macromolecules, vol. 31, No. 25, Dec. 15, 1998, pp. 9093-9095.

* cited by examiner

Primary Examiner—David R Sample
Assistant Examiner—Brieann R Fink
(74) Attorney, Agent, or Firm—Sughrue Mion, PLLC

(57) ABSTRACT

The invention relates to a radically polymerizable sulfur-containing compound having a group represented by formula (1) and at least one selected from among groups represented by formulae (2) to (4), a radically polymerizable sulfur-containing polymer obtained by subjecting the compound to cationic ring-opening (co)polymerization, production process thereof, a composition containing the sulfur-containing compound and/or the sulfur-containing polymer, and a cured product obtained from the composition... (1)(2)(3)(4)... ($R^1$ to $R^6$ each independently represents a hydrogen atom or an alkyl group having 1 to 4 carbon atoms.) The cured product obtained from the radically polymerizable sulfur-containing compound and the radically polymerizable sulfur-containing polymer having a high refractive index is useful as an optical material, especially for lens material.

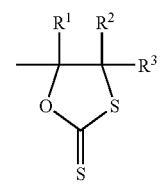

(1)

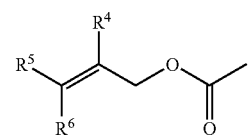

(2)

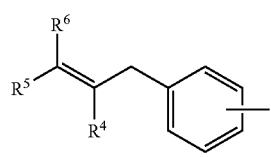

(3)

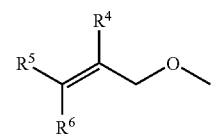

(4)

13 Claims, 6 Drawing Sheets

RADICALLY POLYMERIZABLE SULFUR-CONTAINING COMPOUND AND RADICALLY POLYMERIZABLE SULFUR-CONTAINING POLYMER

CROSS-REFERENCE TO RELATED APPLICATIONS

This is an application filed pursuant to 35 U.S.C. Section 111(a) with claiming the benefit of U.S. provisional application Ser. No. 60/613,239 filed Sep. 28, 2004 under the provision of 35 U.S.C. 111(b), pursuant to 35 U.S.C. Section 119(e)(1).

TECHNICAL FIELD

The invention relates to a radically polymerizable sulfur-containing monomer, a radically polymerizable sulfur-containing polymer, production method thereof, a composition containing the polymer and a cured product thereof.

BACKGROUND ART

As conventional optical materials, especially as resin lens materials, diethylene glycol bis(allylcarbonate) (e.g. CR-39 (product name) manufactured by PPG Industries, Inc.) is known. This resin has various characteristics as plastic lens material, such as excellent impact-resistance, light weight, excellent dyeability, and good workability properties such as cuttability and polishability. However, since the refractive index 1.50 of a lens obtained by radically polymerizing diethylene glycol bis(allylcarbonate) is low as compared with that of inorganic glass (e.g. refractive index of white crown glass is 1.523), in order to obtain optical properties comparable to those of a glass lens, it is necessary to increase the center thickness, peripheral thickness and curvature of the lens, which inevitably renders the whole lens bulky. Accordingly, there has been a demand for resin which enables production of lens having a high refractive index.

Further, known as an organic glass having a higher refractive index than that of a lens obtainable by radically polymerizing diethylene glycol bis(allylcarbonate) is a lens obtainable by curing a resin containing allylester compound which has an allylester group at a terminal and has a structure derived from polyvalent carboxylic acid and polyvalent alcohol is known. This lens has a higher refractive index than that of a lens obtained by curing diethylene glycol bis(allylcarbonate) through radical polymerization and can be easily cured by radical polymerization, however, the refractive index of the lens cannot be said to be sufficiently high.

Known as lens which can solve these problems and realize a high refractive index are a thiourethane lens obtained by curing through reaction of an isocyanate compound with a compound having a mercapto group and further a sulfur-containing acrylate lens obtained by curing a sulfur-containing acrylate compound through radically polymerization.

However, although a thiourethane lens has a high refractive index and a high impact resistance, its production process entails various problems such as toxicity of the raw material isocyanate compound, the odor of the raw material thiol compound, the odor in process of cutting the thiourethane lens and low abrasion resistance of thiourethane lens.

The method for curing diethylene glycol bis(allylcarbonate) or a resin containing allylester compound as mentioned above is radical polymerization, which has been conventionally employed as lens forming method since long ago and therefore, the method is easy to perform. On the other hand, the method for producing thiourethane lens includes mixing an isocyanate compound with a compound having a mercapto group and then pouring the mixture into a mold to cure. Since the method used such a two-liquid type resin, the procedures are complicated. Further, the curing proceeds not through radical polymerization but through addition reaction between an isocyanate group and a mercapto group. In the curing process, it is important to control the temperature and humidity of the room where the step of pouring the mixture solution into the mold is conducted and also, the curing step requires high technique.

With respect to sulfur-containing acrylate lens, many of sulfur-containing acrylate compounds have high viscosity, and also its high reactivity leads to low storage stability. Still further, in performing polymerization reaction, temperature must be carefully controlled to prevent runaway reaction.

On the other hand, a cured product which can serve as an optical material, which is obtained by reacting a bifunctional five-membered ring dithiocarbonate with bifunctional diamine, is described in JP-A-H08-302013. However, since the reaction is two-liquid type, the preparation operation is complicated. Moreover, there is a problem in this technique that after the two solutions are mixed together, the reaction gradually proceeds, which leads to low stability and therefore, a novel resin composition which can serve as optical material has been demanded.

DISCLOSURE OF INVENTION

Accordingly, the object of the invention is to provide a radically polymerizable sulfur-containing monomer which can be used as resin for optical material, a radically polymerizable sulfur-containing polymer, production method thereof, a composition containing the same, and product obtained by curing the composition.

As a result of intensive studies to solve the problems, the present inventors have found out that by using a radically polymerizable sulfur-containing compound having a specific structure or radically polymerizable sulfur-containing polymer, curing can be conducted through radical polymerization and that the lens obtained by such a process can have a refractive index which is higher than that of a conventional lens obtained by curing a resin containing allylester compound, and thus completed the invention.

That is, the invention (I) is a radically polymerizable sulfur-containing compound.

The invention (II) is a radically polymerizable sulfur-containing polymer obtained through cationic ring-opening polymerization of the radically polymerizable sulfur-containing compound of the invention (I).

Further, the invention (III) is a method for producing the radically polymerizable sulfur-containing polymer of the invention (II).

The invention (IV) is a radically polymerizable composition containing the radically polymerizable sulfur-containing compound of the invention (I) and/or the radically polymerizable sulfur-containing polymer of the invention (II).

The invention (V) is a cured product obtained by polymerizing a radically polymerizable composition containing the radically polymerizable sulfur-containing monomer of the invention (I) and/or the radically polymerizable sulfur-containing polymer of the invention (II).

That is, the invention is constituted by the following items.

1. A radically polymerizable sulfur-containing compound comprising a group represented by formula (1)

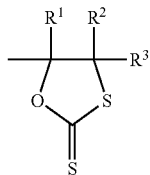

(in the formula, $R^1$ to $R^3$ each independently represents a hydrogen atom or an alkyl group having 1 to 4 carbon atoms) and at least one selected from among groups represented by formulae (2) to (4)

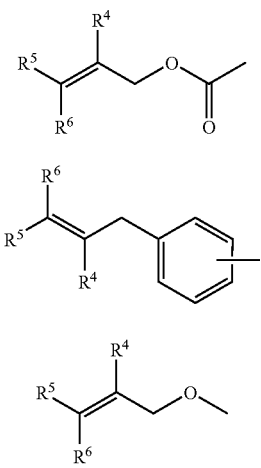

(in the formula, $R^4$ to $R^6$ each independently represents a hydrogen atom or an alkyl group having 1 to 4 carbon atoms)

2. The radically polymerizable sulfur-containing compound as described in 1, which is represented by formula (5)

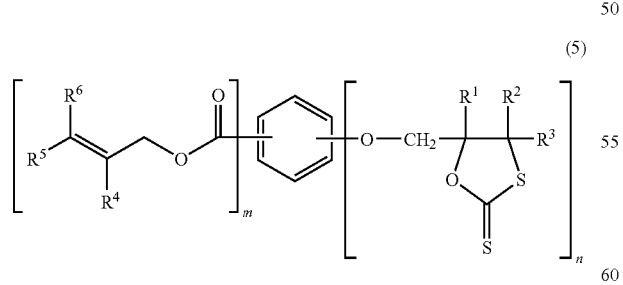

(in the formula, $R^1$ to $R^6$ each independently represents a hydrogen atom or an alkyl group having 1 to 4 carbon atoms, and m and n each independently represents an integer of 1 to 5, with a proviso that $m+n \leqq 6$).

3. The radically polymerizable sulfur-containing compound as described in 1, which is represented by formula (6)

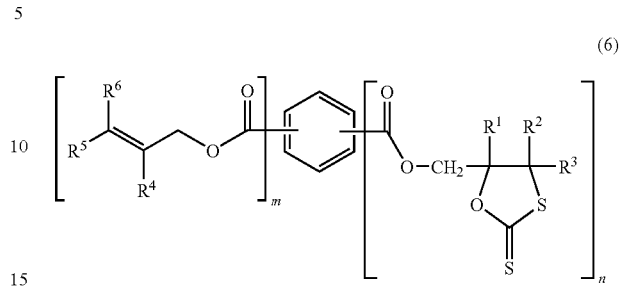

(in the formula, $R^1$ to $R^6$ each independently represents a hydrogen atom or an alkyl group having 1 to 4 carbon atoms, and m and n each independently represents an integer of 1 to 5, with a proviso that $m+n \leqq 6$).

4. The radically polymerizable sulfur-containing compound as described in 1, which is represented by formula (7)

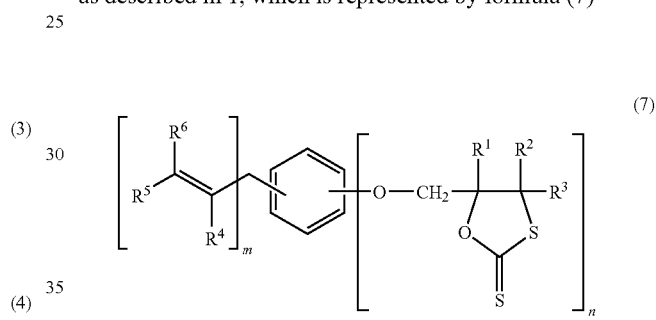

(in the formula, $R^1$ to $R^6$ each independently represents a hydrogen atom or an alkyl group having 1 to 4 carbon atoms, and m and n each independently represents an integer of 1 to 5, with a proviso that $m+n \leqq 6$).

5. The radically polymerizable sulfur-containing compound as described in 1, which is represented by formula (8)

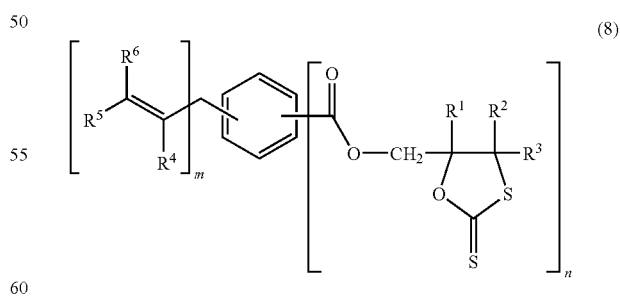

(in the formula, $R^1$ to $R^6$ each independently represents a hydrogen atom or an alkyl group having 1 to 4 carbon atoms, and m and n each independently represent an integer of 1 to 5, with a proviso that $m+n \leqq 6$).

6. The radically polymerizable sulfur-containing compound as described in 1, which is represented by formula (9)

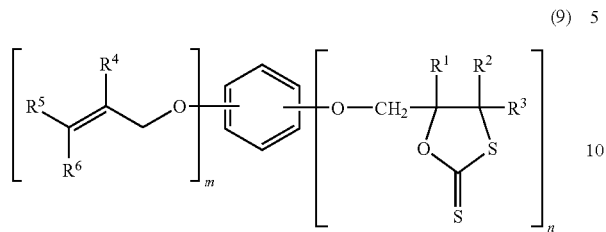

(in the formula, $R^1$ to $R^6$ each independently represents a hydrogen atom or an alkyl group having 1 to 4 carbon atoms, and m and n each independently represents an integer of 1 to 5, with a proviso that m+n≦6).

7. The radically polymerizable sulfur-containing compound as described in 1, which is represented by formula (10)

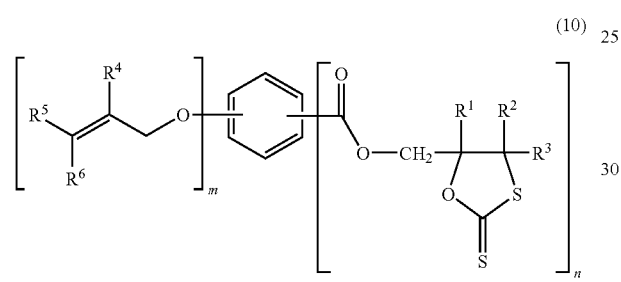

(in the formula, $R^1$ to $R^6$ each independently represents a hydrogen atom or an alkyl group having 1 to 4 carbon atoms, and m and n each independently represents an integer of 1 to 5, with a proviso that m+n≦6).

8. The radically polymerizable sulfur-containing compound as described in any one of 2 to 7, wherein m is 1 and n is 1.

9. The radically polymerizable sulfur-containing compound as described in any one of 1 to 7, wherein all of $R^1$ to $R^6$ are hydrogen atoms.

10. The radically polymerizable sulfur-containing compound as described in any one of 1 to 9, which is used as an optical material.

11. A radically polymerizable sulfur-containing polymer having a group represented by formula (101), which is obtained by subjecting the radically polymerizable sulfur-containing compound described in any one of 1 to 9 to cationic ring-opening polymerization.

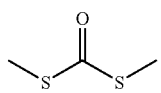

12. The radically polymerizable sulfur-containing polymer as described in 11, which is obtained by subjecting at least one compound described in any one of 1 to 9 and another different compound having a group represented by formula (1) to ring-opening copolymerization

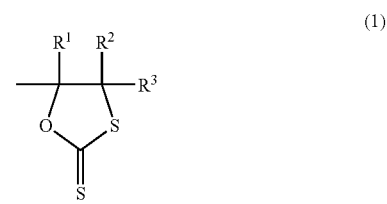

(in the formula, $R^1$ to $R^3$ have the same meanings as defined in 1 above).

13. The radically polymerizable sulfur-containing polymer as described in 11 or 12, having at least one structural unit represented by formula (11)

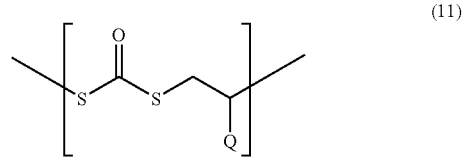

(In the formula, one or more number of Q's are present in the polymer, and the Q in each structural unit independently represents a group represented by any one of formulae (12) to (17)

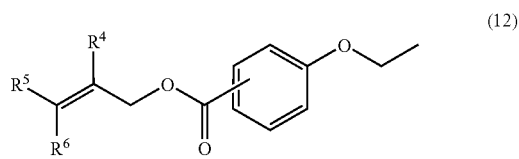

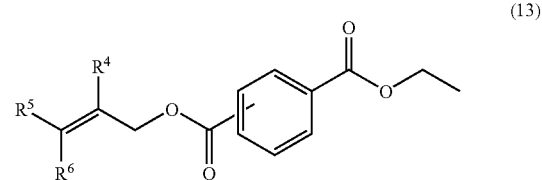

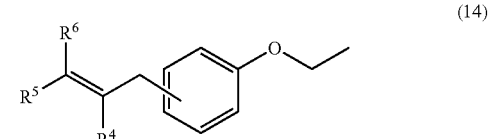

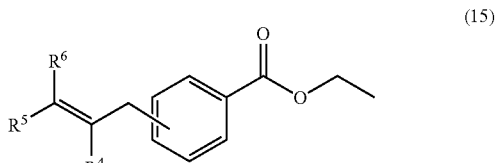

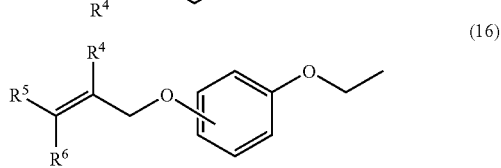

-continued

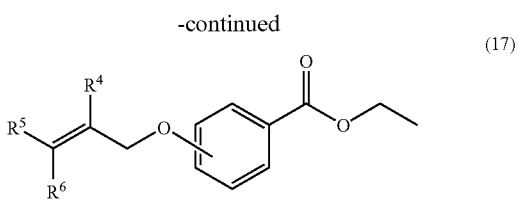

(17)

(in the formula, $R^4$ to $R^6$ each independently represents a hydrogen atom or an alkyl group having 1 to 4 carbon atoms))

14. The radically polymerizable sulfur-containing polymer as described in 13, wherein all of $R^4$ to $R^6$ are hydrogen atoms.

15. The radically polymerizable sulfur-containing polymer as described in any one of 11 to 14, having a weight average molecular weight of 6,000 or less in terms of polystyrene, in measurement by gel permeation chromatography.

16. The radically polymerizable sulfur-containing polymer as described in any one of 11 to 15, which is used for optical material.

17. A method for producing a radically polymerizable sulfur-containing polymer, wherein the radically polymerizable sulfur-containing compound described in any one of 1 to 9 is subjected to cationic ring-opening polymerization in the presence of a catalyst.

18. A method for producing a radically polymerizable sulfur-containing polymer, wherein at least one compound described in any one of 1 to 9 and another different compound having a group represented by formula (1) are subjected to cationic ring-opening copolymerization in the presence of a catalyst

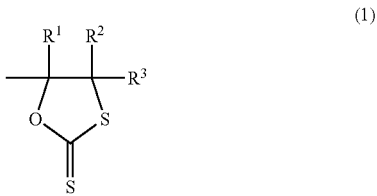

(1)

(in the formula, $R^1$ to $R^3$ have the same meanings as defined in 1 above).

19. The method for producing a radically polymerizable sulfur-containing polymer as described in 17 or 18, wherein the catalyst is at least one selected from the group consisting of methyl trifluoromethane sulfonate, ethyl trifluoromethane sulfonate and trifluoroboron-diethylether adduct.

20. A radically polymerizable composition comprising the radically polymerizable sulfur-containing compound as described in any one of 1 to 9 and/or the radically polymerizable sulfur-containing polymer as described in any one of 11 to 15.

21. The radically polymerizable composition as described in 20, further containing an allylester compound.

22. The radically polymerizable composition as described in 21, wherein the allylester compound is at least one selected from di(meth)allyl phthalate, di(meth)allyl isophthalate and di(meth)allyl terephthalate.

23. The Radically polymerizable Composition as Described in 20 or 21, further comprising at least one compound selected from the group consisting of (meth)allyl benzoate, benzyl(meth)acrylate, phenyl (meth)acrylate, vinyl benzoate, dibenzyl maleate diphenyl maleate, dibenzyl fumarate, diphenyl fumarate, (meth)allyl 2-phenylbenzoate, (meth)allyl 3-phenylbenzoate, (meth)allyl 4-phenylbenzoate, (meth)allyl α-naphthoate, (meth)allyl β-naphthoate, (meth)allyl o-chlorobenzoate, (meth)allyl m-chlorobenzoate, (meth)allyl p-chlorobenzoate, (meth)allyl 2,6-dichlorobenzoate, (meth)allyl 2,4-dichlorobenzoate, (meth)allyl o-bromobenzoate, (meth)allyl m-bromobenzoate, (meth)allyl p-bromobenzoate and di(meth)allyl diphenate.

24. The Radically polymerizable Composition as Described in any one of 20 to 23, further comprising a UV ray absorbent and/or a light stabilizer.

25. The Radically polymerizable Composition as Described in any one of 20 to 24, further comprising an antioxidant.

26. The radically polymerizable composition as described in any one of 20 to 25, further comprising a radical polymerization initiator.

27. The radically polymerizable composition as described in any one of 20 to 26, which is used as an optical material.

28. A cured product obtained by curing the radically polymerizable sulfur-containing compound as described in any one of 1 to 9, the radically polymerizable sulfur-containing polymer as described in any one of 11 to 16 or the radically polymerizable composition as described in any one of 20 to 27.

29. An optical material using the cured product as described in 28.

BEST MODE FOR CARRYING OUT THE INVENTION

Figure 1:
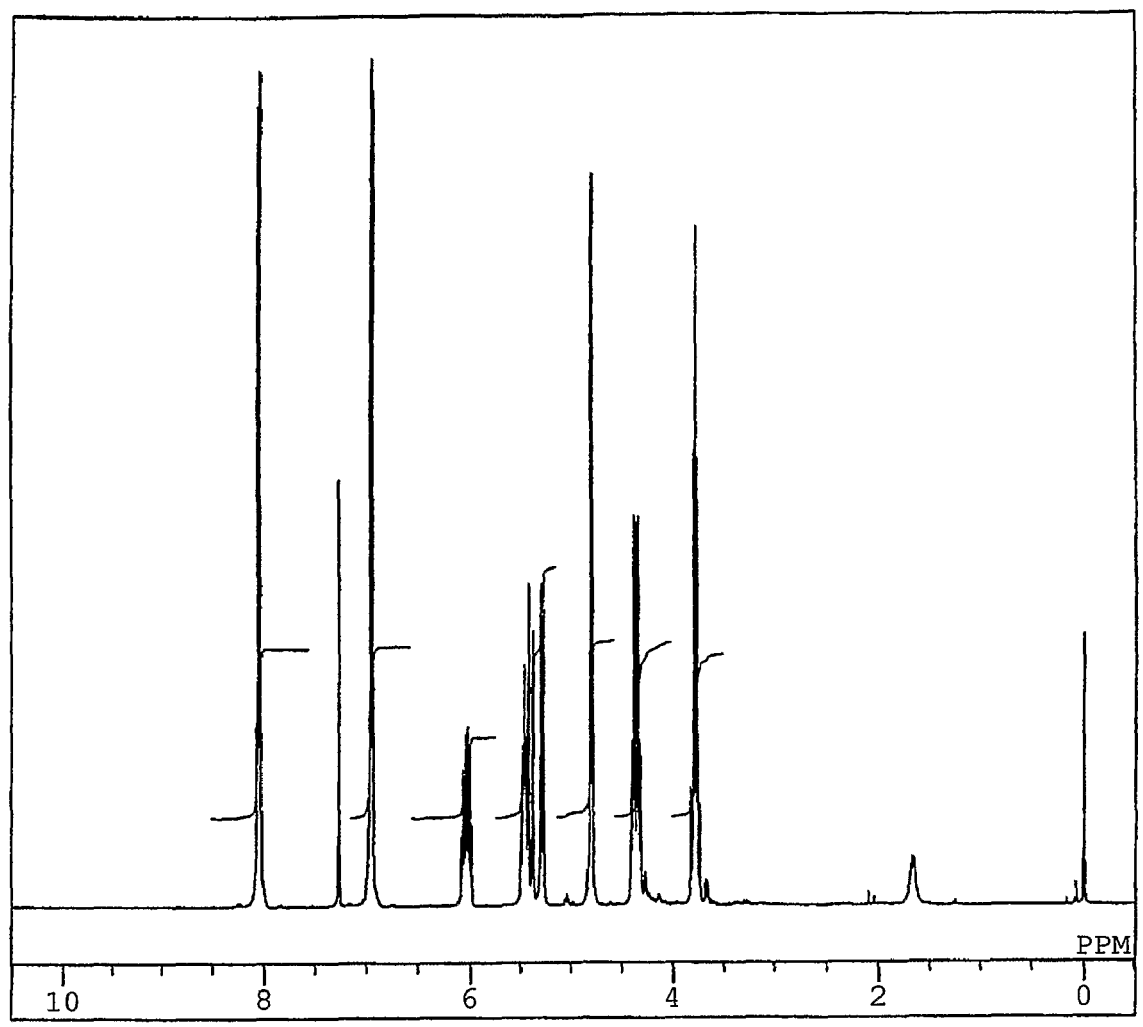
FIG. 1 shows a $^1$H-NMR spectrum of a radical polymerizable sulfur containing compound (Example 1) according to the invention.

Hereinafter, the invention is described in detail. First, the invention (I) is explained. The invention (I) is a radically polymerizable sulfur-containing compound comprising a group (structure) represented by formula (1)

(1)

[Chemical structure of formula (1): 1,3-oxathiolane-2-thione with R¹, R² on one carbon and R³ on adjacent carbon]

(in the formula, $R^1$ to $R^3$ each independently represents a hydrogen atom or an alkyl group having 1 to 4 carbon atoms) and at least one selected from among groups represented by formulae (2) to (4)

(2)

[Chemical structure of formula (2): allylic acetate with $R^4$, $R^5$, $R^6$ substituents]

(3)

[Chemical structure of formula (3): allyl-substituted benzene with $R^4$, $R^5$, $R^6$ substituents]

(4)

[Chemical structure of formula (4): allyl methyl ether with $R^4$, $R^5$, $R^6$ substituents]

(in the formula, $R^4$ to $R^6$ each independently represents a hydrogen atom or an alkyl group having 1 to 4 carbon atoms)

Here, the group (structure) represented by formula (1) is explained.

$R^1$ to $R^3$ each independently represents a hydrogen atom or an alkyl group having 1 to 4 carbon atoms. Examples of alkyl group having 1 to 4 carbon atoms include methyl group, ethyl group, n-propyl group, isopropyl group, n-butyl group, sec-butyl group, isobutyl group and t-butyl group. In case of using the invention in the field where a high refractive index is required, it is preferable that the number of carbon atoms in the alkyl group or the number of the alkyl groups be small. The most preferably, all of $R^1$ to $R^3$ are hydrogen atoms.

The phrase "each independently represents" in "$R^1$ to $R^3$ each independently represents" means that each of $R^1$ to $R^3$ present in formula (1) may represent a group different from each other. For example, when $R^1$ is a hydrogen atom, $R^2$ and $R^3$ may be methyl groups. The phrase has the same meaning in definition of the other formulae.

Next, the groups (structures) represented by formulae (2) to (4) are explained.

$R^4$ to $R^6$ in formulae (2) to (4) each independently represents a hydrogen atom or an alkyl group having 1 to 4 carbon atoms. Examples of alkyl group having 1 to 4 carbon atoms include methyl group, ethyl group, n-propyl group, isopropyl group, n-butyl group, sec-butyl group, isobutyl group and t-butyl group. In light of polymerizability, it is preferable that the number of carbon atoms in the alkyl group or the number of the alkyl groups be small. The most preferably, all of $R^4$ to $R^6$ are hydrogen atoms.

Examples of the radically polymerizable sulfur-containing compound of the invention include compounds represented by formulae (5) to (10) Although m and n each may independently represent an integer of 1 to 5, it is preferable that n be 1 in light of preventing gelation during the cationic ring-opening polymerization. Further, it is preferable that m be 1 or 2 in light of curability in radical polymerization process and impact resistance of cured product.

(5)

[Chemical structure of formula (5)]

(in the formula, $R^1$ to $R^6$ each independently represents a hydrogen atom or an alkyl group having 1 to 4 carbon atoms, and m and n each independently represent an integer of 1 to 5, with a proviso that $m+n \leq 6$), (6)

[Chemical structure of formula (6)]

(in the formula, $R^1$ to $R^6$ each independently represents a hydrogen atom or an alkyl group having 1 to 4 carbon atoms, and m and n each independently represent an integer of 1 to 5, with a proviso that $m+n \leq 6$), (7)

[Chemical structure of formula (7)]

(in the formula, $R^1$ to $R^6$ each independently represents a hydrogen atom or an alkyl group having 1 to 4 carbon atoms, and m and n each independently represent an integer of 1 to 5, with a proviso that $m+n \leq 6$)

(8)

[Chemical structure of formula (8)]

(in the formula, $R^1$ to $R^6$ each independently represents a hydrogen atom or an alkyl group having 1 to 4 carbon atoms, and m and n each independently represent an integer of 1 to 5, with a proviso that m+n≦6),

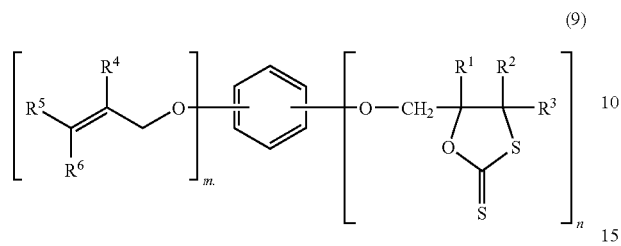

(9)

(in the formula, $R^1$ to $R^6$ each independently represents a hydrogen atom or an alkyl group having 1 to 4 carbon atoms, and m and n each independently represent an integer of 1 to 5, with a proviso that m+n≦6),

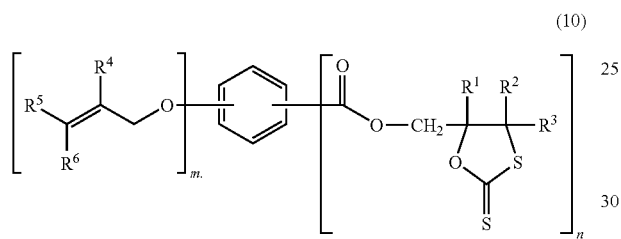

(10)

(in the formula, $R^1$ to $R^6$ each independently represents a hydrogen atom or an alkyl group having 1 to 4 carbon atoms, and m and n each independently represent an integer of 1 to 5, with a proviso that m+n≦6).

Next, the method for producing the radically polymerizable sulfur-containing compound of the invention (I) is explained.

The method for producing the radically polymerizable sulfur-containing compound of the invention can be divided into a step of synthesizing the group (structure) represented by formula (1) and a step of synthesizing the group (structure) represented by formulae (2) to (4). Either of these two steps may precede the other step.

The synthesis method of the structure represented by formula (1) is described.

As a method of preparing the structure represented by formula (1) in the radically polymerizable sulfur-containing compound, a method where an epoxy group is reacted with carbon disulfide in the presence of an alkali metal salt or an alkali earth metal salt can be mentioned. Specifically, the structure can be obtained according to the method described in JP-A-H05-247027 (the term "JP-A-" means an unexamined Japanese patent application laid-open No.)

The epoxy group can be prepared according to a known method, for example by reacting a carboxylic acid group or a hydroxyl group with a halohydrin such as epichlorohydrin.

The group represented by formula (1) can be prepared by reacting an epoxy group with carbon disulfide in the presence of an alkali metal salt or an alkali earth metal salt. However, a compound having a group where an oxygen atom and a sulfur atom are present at positions different from the positions of those atoms in formula (1) is sometimes produced as a side product. Examples thereof include the groups represented by formulae (18) to (23).

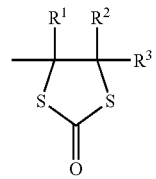

(18)

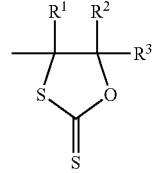

(19)

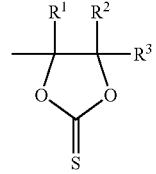

(20)

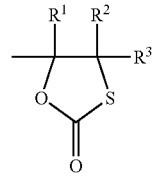

(21)

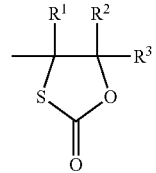

(22)

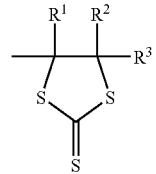

(23)

(In the formulae, $R^1$ to $R^3$ each independently represents a hydrogen atom or an alkyl group having 1 to 4 carbon atoms).

The compound having such a group as side product may be removed by a known purification method such as column purification, distillation purification or adsorption purification, or the reaction product may be used without being purified.

Next, the method for synthesizing a polymerizable functional group represented by formula (2) is explained.

A polymerizable functional group represented by formula (2) can be synthesized by esterifying a compound having a carboxylic acid group and an alcohol represented by formula (24).

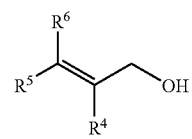

(24)

(In the formula, $R^4$ to $R^6$ each independently represent a hydrogen atom or an alkyl group having 1 to 4 carbon atoms.)

Another synthesis method is transesterification reaction between a compound having an ester group and an alcohol represented by formula (24).

Examples of the compound having carboxylic acid group include aromatic carboxylic acids such as phthalic acid, phthalic anhydride, isophthalic acid, terephthalic acid, trimellitic acid, trimellitic anhydride, pyromellitic acid, pyromellitic anhydride, salicylic acid, 3-hydroxybenzoic acid and 4-hydroxybenzoic acid; carboxylic acids of alicyclic hydrocarbon such as 1,2-cyclohexanedicarboxylic acid, 1,3-cyclohexanedicarboxylic acid, 1,4-cyclohexanedicarboxylic acid, 3,6-methylene-1,2-cyclohexanedicarboxylic acid, 1-cyclohexene-1,2-dicarboxylic acid, chlorendic acid, chlorendic anhydride and endic acid;

unsaturated aliphatic dicarboxylic acids such as maleic acid, maleic anhydride and fumaric acid;

saturated aliphatic dicarboxylic acids such as malonic acid, succinic acid and glutaric acid.

Examples of the compound having an ester group include ester compound obtained from the above-mentioned carboxylic acids and alcohols.

Further, the method for synthesizing a polymerizable functional group represented by formula (3) is explained.

A polymerizable functional group (structure) represented by formula (3) can be synthesized, for example, by reacting a halogenated compound represented by formula (25) with a compound having a phenolic hydroxyl group and then subjecting the reaction product to Claisen Rearrangement.

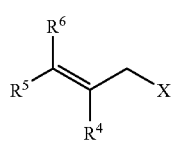
(25)

(In the formula, $R^4$ to $R^6$ each independently represents a hydrogen atom and an alkyl group having 1 to 4 carbon atoms. X represents a chlorine atom, a bromine atom or an iodine atom.)

To be more specific about the above described method, the structure wherein $R^4$ to $R^6$ are hydrogen atoms may be obtained by reaction scheme represented by formula (26).

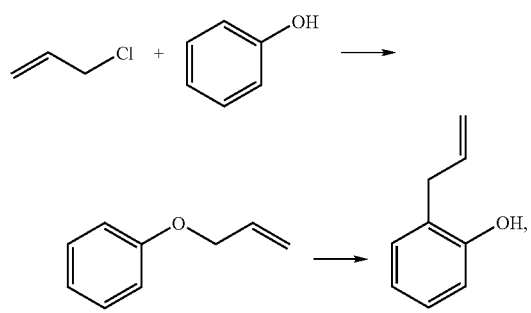
(26)

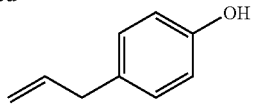

Alternatively, a polymerizable functional group represented by formula (3) can be synthesized through Friedel-Crafts reaction between a halogenated compound represented by formula (25) and a phenyl group.

Furthermore, the method for synthesizing a polymerizable functional group (structure) represented by formula (4) is explained.

A polymerizable functional group (structure) represented by formula (4) can be synthesized, for example, by etherifying a halogenated compound represented by formula (25) and a compound having a hydroxyl group.

Next, the polymerizable sulfur-containing polymer of the invention (II) is explained.

The polymerizable sulfur-containing polymer of the invention (II) is a radically polymerizable sulfur-containing polymer comprising a group represented by formula (101) which is obtained by subjecting a group of formula (1) in the radically polymerizable sulfur-containing compound to cationic ring-opening polymerization

(101)

and at least one kind selected from the group consisting of formulae (2) to (4).

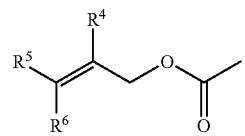
(2)

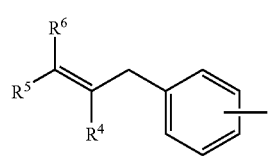
(3)

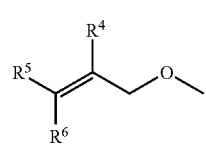
(4)

(In the formulae, $R^4$ to $R^6$ each independently represents a hydrogen atom or an alkyl group having 1 to 4 carbon atoms.)

In formulae (2) to (4), $R^4$ to $R^6$ each independently represents a hydrogen atom or an alkyl group having 1 to 4 carbon atoms. Examples of alkyl group having 1 to 4 carbon atoms include methyl group, ethyl group, n-propyl group, n-isopropyl group, n-butyl group, sec-butyl group, isobutyl group and t-butyl group. In light of polymerizability, the smaller the number of carbon atoms in the alkyl group or the number of alkyl groups, the more preferable. The most preferred is a case where all of $R^4$ to $R^6$ are hydrogen atoms.

Examples of radically polymerizable sulfur-containing polymer of the invention (II) include a polymer having at least one structure represented by formula (11)

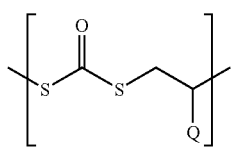
(11)

(In the formula, Q of each structural unit, which unit is singularly or plurally present in the polymer, independently represents at least one species of formulae (12) to (17).

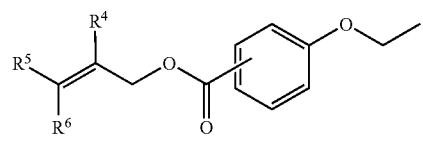
(12)

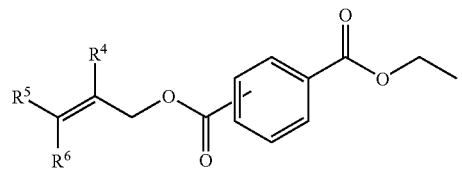
(13)

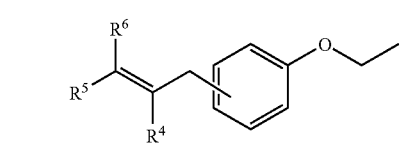
(14)

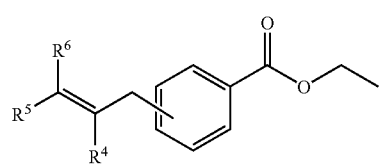
(15)

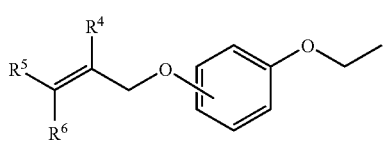
(16)

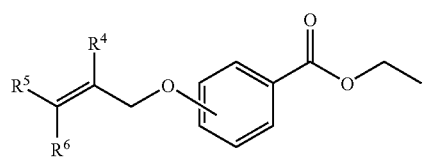
(17)

(In the formula, $R^4$ to $R^6$ each independently represents a hydrogen atom or an alkyl group having 1 to 4 carbon atoms.)

The radically polymerizable sulfur-containing polymer of the invention includes at least one structural unit of formula (11) in the polymer structure. Therefore, when the radically polymerizable sulfur-containing polymer is a random polymer, a graft polymer or a block polymer, the polymer include other structural units in addition to formula (11).

Examples of other structural units of the polymer include those represented by formulae (102) to (109).

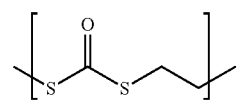
(102)

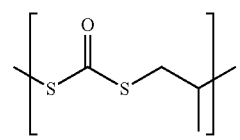
(103)

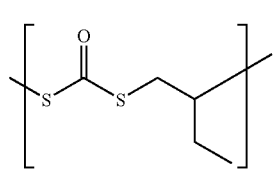
(104)

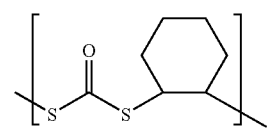
(105)

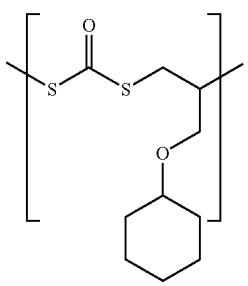
(106)

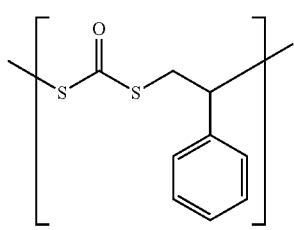
(107)

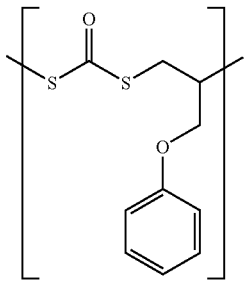
(108)

-continued

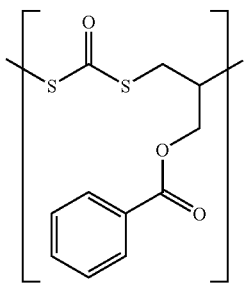
(109)

There are no particular limitations on the molecular weight distribution, the number average molecular weight and the weight average molecular weight. The polymer of the invention can be dissolved in a polymerizable compound which is liquid at room temperature (reactive diluent) to thereby form a polymerizable composition and then cured by cast-molding. In light of working properties such as casting speed in case of conducting cast-molding or filtration speed in case of conducting filtration, the viscosity of the polymerizable composition has importance. From an economical viewpoint, it is preferred that the casting speed or the filtration speed be high. The lower the viscosity of the polymerizable composition, the higher the casting speed or the filtration speed. In order to render the viscosity of the polymerizable composition low, it is preferred that the molecular weight of the polymer of the invention to be blended in the composition be low.

In order to render the viscosity of the polymerizable composition low, it is preferable that the molecular weight of the polymer of the invention be 10000 or less in terms of polystyrene when measured by gel permeation chromatography, more preferably 6000 or less, even more preferably 3000 or less.

Further, production method for the polymerizable sulfur-containing polymer of the invention (III) is described.

In the invention (III), the radically polymerizable sulfur-containing polymer of the invention (II) can be obtained by subjecting a group of formula (1) in the radically polymerizable sulfur-containing compound of the invention (I) to cationic ring-opening polymerization in the presence of a catalyst.

Alternatively, a method of producing the radically polymerizable sulfur-containing polymer having group represented by formula (101) which is obtained by subjecting the radically polymerizable sulfur-containing compound of the invention (I) and another different compound having a group (structure) of formula (1) to cationic ring-opening copolymerization in the presence of a catalyst is provided.

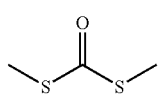
(101)

A specific example of cationic ring-opening polymerization in the production method of the polymerizable sulfur-containing polymer of the invention (III) is shown in the formula below.

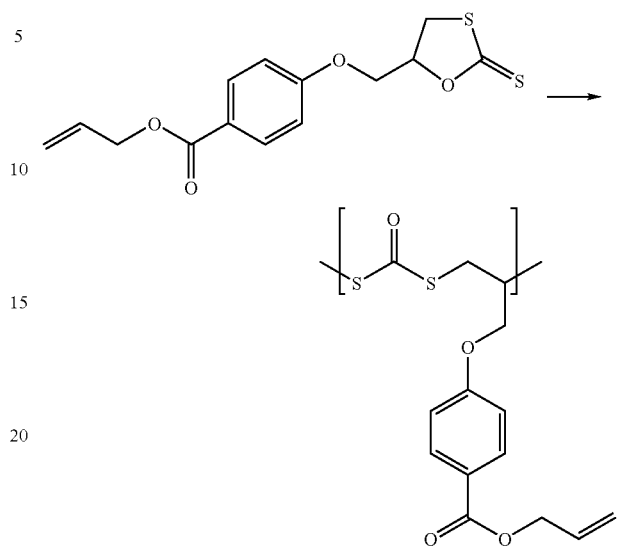
(27)

Also, a specific example of copolymerization is shown in the formula below.

(28)

Structure 1    Structure 2
random polymer including Structures 1 and 2

As a compound having a group represented by formula (1) and also having a methacryl group as a polymerizable functional group, a compound represented by formula (110) is known (for example, see JP-A-9-59324).

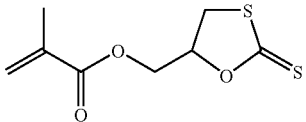
(110)

With a methacryl group, any of radical polymerization, cationic polymerization and anionic polymerization can be conducted.

In the production process of the radically polymerizable sulfur-containing polymer of the invention (III), the polymer is produced by using a cationic polymerization catalyst. If the above compound (110) is subjected to cationic polymerization reaction under the same condition as in the invention, cationic polymerization of methacryl group and ring-opening polymerization of the group represented by formula (1) would occur concurrently, which would lead to gelation and as a result, a radically polymerizable sulfur-containing polymer could not be produced. Therefore, it is not preferable to use the compound as a copolymerization monomer in the cationic ring-opening copolymerization.

As compound having a group of formula (1) other than the compound of the invention (1), which is used in the cationic ring-opening copolymerization, a compound having no cationically polymerizable group other than a group represented by formula (1) is preferred. Examples thereof include compounds represented by formulae (111) to (118).

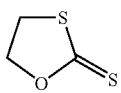
(111)

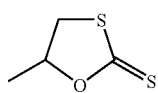
(112)

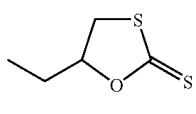
(113)

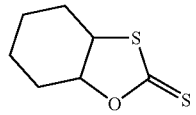
(114)

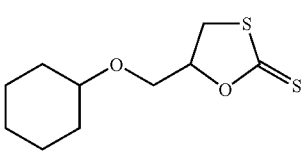
(115)

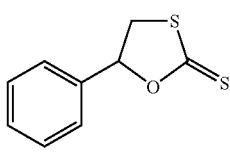
(116)

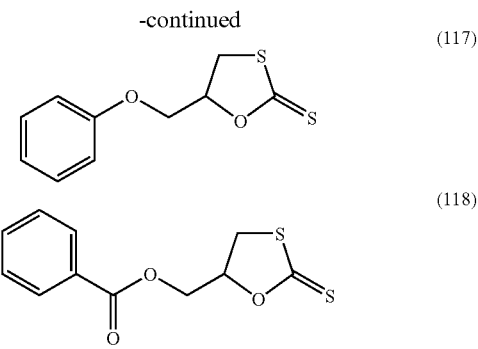

(117)

(118)

In a case where polymer is produced by using a compound having two or more groups of formula I in one molecule according to the invention, gelation is more likely to occur during the production process than in a case using a compound having only one group of formula (1) in one molecule according to the invention. In order to produce the polymer without gelation, it is preferable that the amount of the compound having two or more groups of formula (1) in one molecule according to the invention be 10 mass % or less, more preferably 5 mass % or less, even more preferably 2 mass % or less based on the total monomer amount.

Examples of the catalysts which used for the production of the radical polymerizable sulfur containing polymer of the invention include boron trifluoride etherate; alkyl trifluoromethanesulfonates such as methyl trifluoromethanesulfonate, ethyl trifluoromethanesulfonate and n-propyl trifluoromethanesulfonate; dialkylesters of sulfuric acid such as dimethyl sulfate and diethyl sulfate; alkyl p-toluenesulfonates such as methyl p-toluenesulfonate and ethyl p-toluenesulfonate; quaternary ammonium salt, phosphonium salt, sulfonium salt, diazonium salt and iodonium salt.

Examples of quaternary ammonium salts include tetrabutylammonium tetrafluoroborate, tetrabutylammonium hexafluorophosphate, tetrabutylammonium hydrogen sulfate, tetraethylammonium tetrafluoroborate, tetraethylammonium p-toluenesulfonate, N-benzyl-N,N-dimethyl anilinium antimony hexafluoride, N-benzyl-N,N-dimethyl anilinium boron tetrafluoride, N-(4-methoxybenzyl)-N,N-dimethyl anilinium antimony hexafluoride, N-benzyl-N,N-dimethyl toluidinium antimony hexafluoride, N-benzyl pyridinium antimony hexafluoride, N-benzyl-4-cyanopyridinium antimony hexafluoride and 4-cyano-N-(4-methoxybenzyl) pyridinium antimony hexafluoride.

Examples of phosphonium salts include ethyltriphenylphosphonium antimony hexafluoride and tetrabutylphosphonium antimony hexafluoride.

Examples of sulfonium salts include triphenylsulfonium boron tetrafluoride, triphenylsulfonium antimony hexafluoride, triphenylsulfonium arsenic hexafluoride, tri(4-methoxyphenyl)sulfonium arsenic hexafluoride, diphenyl(4-phenylthiophenyl)sulfonium arsenic hexafluoride, ADEKA OPTON SP-150 (trade name, product of Asahi Denka Co., Ltd.; counter ion: $PF_6$), ADEKA OPTON SP-170 (trade name, product of Asahi Denka Co., Ltd.; counter ion: $SbF_6$), ADEKA OPTON CP-66 (trade name, product of Asahi Denka Co., Ltd.; counter ion: $SbF_6$), ADEKA OPTON CP-77 (trade name, product of Asahi Denka Co., Ltd.; counter ion: $SbF_6$), San-Aid SI-60L (trade name, product of SANSHIN CHEMICAL INDUSTRY CO., LTD.; counter ion: $SbF_6$), San-Aid SI-80L (trade name, product of SANSHIN CHEMICAL INDUSTRY CO., LTD.; counter ion: $SbF_6$), San-Aid SI-100L (trade name, product of SANSHIN CHEMICAL INDUSTRY CO., LTD.; counter ion: $SbF_6$), San-Aid SI-150 (trade name, product of SANSHIN CHEMICAL INDUSTRY CO., LTD.; counter ion: $SbF_6$), CYRACURE UVI-6974 (trade name, product of Union Carbide Corporation; counter ion: $SbF_6$), CYRACURE UVI-6990 (trade name, product of Union Carbide Corporation; counter ion: $PF_6$), UVI-508 (trade name, product of General Electric Company), UVI-509 (trade name, product of General Electric Company), FC-508 (trade name, product of MINNESOTA MINING & MANUFACTURING CORPORATION), FC-509 (trade name, product of MINNESOTA MINING & MANUFACTURING CORPORATION), CD-1010 (trade name, product of Sartomer Company, Inc.), CD-1011 (trade name, product of Sartomer Company, Inc.) and CI Series (trade name, product of NIPPON SODA CO., LTD.; counter ion: $PF_6$, $SbF_6$).

Specific examples of diazonium salts include AMERICURE produced by American can (counter ion: $BF_4$) and ULTRASET produced by Asahi Denka Co., Ltd. (counter ion: $BF_4$, $SbF_6$).

Specific examples of iodonium salts include diphenyliodonium arsenic hexafluoride, di(4-chlorophenyl)iodonium arsenic hexafluoride, di(4-bromophenyl)iodonium arsenic hexafluoride, phenyl(4-methoxyphenyl)iodonium arsenic hexafluoride, UVE Series produced by General Electric Company, FC Series produced by MINNESOTA MINING & MANUFACTURING CORPORATION, UV-9310C produced by Toshiba Silicones (counter ion: $SbF_6$) and Photoinitiator 2074 produced by Rhone-Poulenc Ltd. (counter ion: $(C_6F_5)_4B$).

One of these catalysts may be used singly or two or more of them may be used in combination.

The use amount of the catalyst is 0.01 to 20 mass %, preferably 0.1 to 10 mass %, more preferably 0.5 to 5 mass %, based on the total monomer mass. If the amount of the catalyst is less than 0.01 mass %, the ring-opening polymerization may procrastinate, while if it exceeds 20 mass %, it is economically disadvantageous. Since the number average molecular weight and the weight average molecular weight of a polymer are influenced by the catalyst amount, the use amount of the catalyst needs to be determined in consideration of that aspect.

Further, the catalytic activity may be enhanced by adding a Lewis acid such as aluminum chloride, titanium tetrachloride or tin tetrachloride to the catalyst.

The radically polymerizable sulfur-containing polymer of the invention can be produced by subjecting a functional group of formula (1) to cationic ring-opening polymerization, without polymerizing radically polymerizable functional groups of formulae (2) to (4).

For the purpose of subjecting a functional group of formula (1) to ring-opening polymerization without polymerizing radically polymerizable functional groups of formulae (2) to (4), a polymerization inhibitor may be used in the process of producing the polymer.

Kinds of polymelization inhibitors include quinones such as p-benzoquinone, naphthoquinone and 2,5-diphenyl-p-benzoquinone; polyhydric phenols such as hydroquinone, p-t-butylcatechol and 2,5-di-t-butylhydroquinone; phenols such as hydroquinone monomethyl ether, di-t-butyl-para-cresol and α-naphthol.

In addition, production of the radically polymerizable sulfur containing polymer of the invention may be conducted without a solvent, or may be conducted using a solvent.

Examples of the solvents include aromatic hydrocarbons such as benzene, toluene and xylene; ethers such as diethyl ether, dimethoxyethane, methoxyethylether, tetrahydrofuran and 1,4-dioxane; esters such as ethyl acetate and butyl acetate; ketones such as acetone and methyl ethyl ketone; halogenated hydrocarbons such as chlorobenzene, chloroform, methylene chloride, dichloroethane and carbon tetrachloride. One of these solvent may be used singularly, or two or more of them may be used in a mixture.

The reaction temperature is 20 to 180° C., preferably 40 to 150° C., more preferably 60 to 120° C. If the temperature exceeds 180° C., side-reactions such as gelation occurs in many cases, while if the temperature is less than 20° C., the reaction often procrastinates, which is not preferred.

The radically polymerizable sulfur-containing polymer of the invention may be used without purification or with purification when necessary.

Examples of purification methods include adsorption treatment using an adsorbent and reprecipitation method.

Moreover, although some monomers used in the reaction sometimes remain in the resultant polymer, the polymer may be used as is or may be used after removing the monomers through the purification as above described.

Furthermore, although some compounds each having a group each represented by one of formulae (18) to (23) are by-produced in the polymerization process and remain in the resultant polymer, the polymer may be used as is or may be used after removing the compounds through the purification as above described.

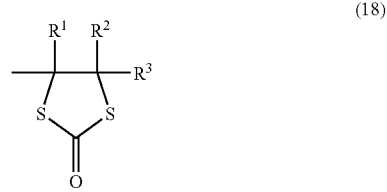

(18)

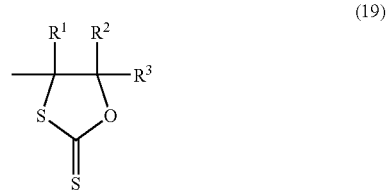

(19)

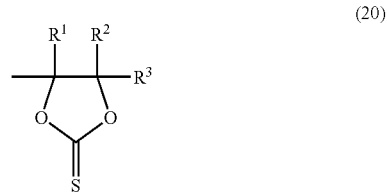

(20)

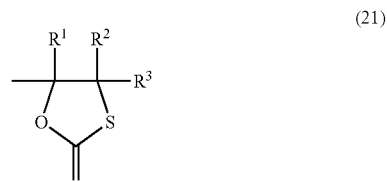

(21)

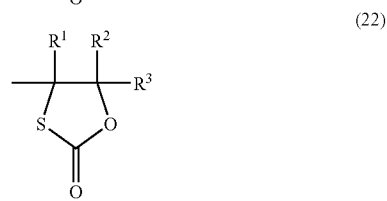

(22)

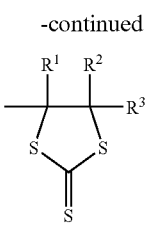

(In the formulae, $R^1$ to $R^3$ each independently represent a hydrogen atom or an alkyl group having 1 to 4 carbon atoms.)

Next, the invention (IV) is described.

The invention (IV) is a radically polymerizable composition containing the radically polymerizable sulfur-containing compound of the invention (I) and/or the radically polymerizable sulfur-containing polymer of the invention (II).

In the composition of the invention, other radically polymerizable compounds may be contained. Examples of other radically polymerizable compounds include compounds having a radically polymerizable group other than the radically polymerizable sulfur-containing compound of the invention (I) and the radically polymerizable sulfur-containing polymer of the invention (II).

Specific examples of other radical polymerizable compounds include allyl esters such as di(meth)allyl-phthalate, di(meth)allyl isophthalate, di(meth)allyl terephthalate, (meth)allyl benzoate, (meth)allyl α-Naphthoate, (meth)allyl β-Naphthoate, (meth)allyl 2-phenylbenzoate, (meth)allyl 3-phenylbenzoate, (meth)allyl 4-phenylbenzoate, (meth)allyl o-chlorobenzoate, (meth)allyl m-chlorobenzoate, (meth)allyl p-chlorobenzoate, (meth)allyl o-bromobenzoate, (meth)allyl m-bromobenzoate, (meth)allyl p-bromobenzoate, (meth)allyl 2,6-dichlorobenzoate, (meth)allyl 2,4-dichlorobenzoate, (meth)allyl 2,4,6-tribromobenzoate, di(meth)allyl 1,4-cyclohexane-dicarboxylate, di(meth)allyl 1,3-cyclohexane-dicarboxylate, di(meth)allyl 1,2-cyclohexane-dicarboxylate, di(meth)allyl 1-cyclohexene-1,2-dicarboxylate, di(meth)allyl 3-methyl-1,2-cyclohexane-dicarboxylate, di(meth)allyl 4-methyl-1,2-cyclohexane-dicarboxylate, di(meth)allyl endate, di(meth)allyl chlorendate, di(meth)allyl 3,6-methylene-1,2-cyclohexane-dicarboxylate di(meth)allyl trimellitate and di(meth)allyl diphenate;

maleic acid diesters/fumaric acid diesters such as dibenzyl maleate, dibenzyl fumarate, diphenyl maleate, diphenyl fumarate, dibutyl maleate, dibutyl fumarate, dimethoxyethyl maleate and dimethoxyethyl fumarate;

(meth)acrylates such as methyl(meth)acrylate, ethyl (meth)acrylate, butyl(meth)acrylate, 2-ethylhexyl(meth)acrylate, phenyl(meth)acrylate, benzyl(meth)acrylate, isobornyl (meth)acrylate, trimethylolpropane tri(meth)acrylate and ethylene glycol di(meth)acrylate;

aromatic vinyl compounds such as styrene, α-styrene, methoxystyrene and divinylbenzene;

vinylesters of aliphatic carboxylic acid such as vinyl acetate, vinyl propionate, vinyl butyrate, vinyl pivalate, vinyl stearate and vinyl caproate;

alicyclic vinylesters such as cyclohexane carboxylic acid ester;

aromatic vinylesters such as vinyl benzoate and vinyl t-butylbenzoate;

allyl carbonate compounds such as polyethyleneglycol bis (allyl)carbonate resin represented by diallyl carbonate, diethyleneglycol bisallyl carbonate and CR-39(trade name, product of PPG Industries, Inc.).

The blending amount of these radically polymerizable compounds is not particularly limited. In a case where the composition of the invention is used as a polymerizable compound for plastic lens and curing is conducted by cast molding, it is preferable that the viscosity of the composition at the temperature when the compound is poured into a mold be 600 mPa·s or less, more preferably 300 mPa·s or less, even more preferably 200 mPa·s or less in consideration for pourability into the mold and therefore, radically polymerizable monomers may be blended in the composition at an appropriate amount for the purpose of adjusting the viscosity. The viscosity is a value which is determined in accordance with JIS Z8803.

In the composition of the invention, ultraviolet absorber, antioxidant, mold release agent, colorant and radical polymerization initiator may be blended in.

Specific examples of the ultraviolet absorbers include triazoles such as 2-(2'-hydroxy-tert-butylphenyl)benzotriazole;

benzophenones such as 2,4-dihydroxybenzophenone;

salicilates such as 4-tert-butylphenyl salicilate; and hindered amines such as bis-(2,2,6,6-tetramethyl-4-piperidinyl)sebacate.

The blending amount of ultraviolet absorber depends on the kinds, amounts and the like of the other components to be blended in the composition, however, it is generally preferable that the amount of ultraviolet absorber be 0.01 to 2 parts by mass, more preferably 0.03 to 1.7 parts by mass, most preferably 0.05 to 1.4 parts by mass based on 100 parts by mass of all the curable components in the radically polymerizable composition. If the amount of ultraviolet absorber is less than 0.01 parts by mass, sufficient effects cannot be expected, while if it exceeds 2 parts by mass, it is economically disadvantageous.

Examples of the antioxidants include phenol antioxidants such as 2,6-di-tert-butyl-4-methylphenol, tetrakis-[methylene-3-(3',5'-di-tert-butyl-4-hydroxyphenyl)propionate] methane; sulfur-based antioxidants such as dilauryl-3,3'-thiodipropionate; and phosphorus-based antioxidants such as trisnonylphenyl phosphite.

The blending amount of antioxidant depends on the kinds, amounts and the like of the other components to be blended in the composition, however, it is generally preferable that the amount of antioxidant be 0.01 to 5 parts by mass, more preferably 0.05 to 4 parts by mass, most preferably 1 to 3 parts by mass based on 100 parts by mass of all the curable components in the radically polymerizable composition. If the amount of antioxidant is less than 0.01 parts by mass, sufficient effects cannot be expected, while if it exceeds 5 parts by mass, it is economically disadvantageous.

Examples of mold release agent include stearic acid, butyl stearate, zinc stearate, stearic acid amide, fluorine compounds and silicon compounds.

The blending amount of mold release agent depends on the kinds, amounts and the like of the other components to be blended in the composition, however, it is generally preferable that the amount of mold release agent be 0.01 to 2 parts by mass, more preferably 0.03 to 1.7 parts by mass, most preferably 0.05 to 1.4 parts by mass based on 100 parts by mass of all the curable components in the radically polymerizable composition. If the amount mold release agent is less than 0.01 parts by mass, sufficient effects cannot be expected, while if it exceeds 2 parts by mass, it is economically disadvantageous.

Examples of the coloring agents include organic pigments such as anthraquinone series, azo series, carbonium series, quinoline series, quinone imine series, indigoid series and phthalocyanine series; organic dyes such as azoic dye and sulfide dye; inorganic pigments such as titanium yellow, yellow iron oxide, zinc yellow, chrome orange, molybdenum red, cobalt violet, cobalt blue, cobalt green, chromium oxide, titanium oxide, zinc sulfide, carbon black. The blending quantity of these is not limited specifically.

Examples of the radical polymerization initiators include azo-based compounds such as 2,2'-azo-bis-iso-butyronitrile and 2,2'-azo-bis-iso-valeronitrile;

ketone peroxides such as methyl ethyl ketone peroxide, methyl isobutyl ketone peroxide and cyclohexanone peroxide (e.g. PERHEXA H: product of NOF CORPORATION);

diacyl peroxides such as dibenzoyl peroxide (e.g. NYPER BO: product of NOF CORPORATION), didecanoyl peroxide and dilauroyl peroxide (e.g. PEROYL L: product of NOF CORPORATION); dialkyl peroxides such as dicumyl peroxide (e.g. PERCUMYL D: product of NOF CORPORATION), t-butylcumylperoxide (e.g. PERBUTYLC: product of NOF CORPORATION)and di-t-butyl peroxide (e.g. PERBUTYL D: product of NOF CORPORATION);

peroxyketals such as 1,1-di-t-butylperoxycyclohexane (e.g. PERHEXA C-80(S): product of NOF CORPORATION), 2,2-di(t-butylperoxy)butane e.g. PERHEXA 22: product of NOF CORPORATION) and 1,1-di(t-hexylperoxy)-3,3,5-trimethylcyclohexane (e.g. PERHEXA TMH): product of NOF CORPORATION);

peroxy esters such as t-butyl peroxypivalate (e.g. PERBUTYL PV: product of NOF CORPORATION), t-butyl peroxy-2-ethylhexanoate e.g. PERBUTYL O: product of NOF CORPORATION), t-butyl peroxyisobutyrate (e.g. KAYAESTER I: product of Kayaku Akzo Corporation), di-t-butyl peroxyhexahydroterephthalate (e.g. KAYAESTER HTP-65W: product of Kayaku Akzo Corporation), t-butyl peroxy-3,5,5-trimethylhexanoate (e.g. TRIGONOX 42: product of Kayaku Akzo Corporation), t-butyl peroxyacetate (e.g. KAYABUTYL A-50T: product of Kayaku Akzo Corporation), t-butyl peroxybenzoate (e.g. PERBUTYL Z: product of NOF CORPORATION), di-t-butyl peroxytrimethyladipate (e.g. KAYAESTER TMA: product of Kayaku Akzo Corporation), 1,1,3,3-tetramethylbutylperoxy-2-ethylhexanoate (e.g. PEROCTA O: product of NOF CORPORATION) and t-hexylperoxy-2-ethylhexanoate (e.g. PERHEXYL 0: product of NOF CORPORATION);

peroxycarbonates such as di-isopropyl peroxydicarbonate (e.g. PEROYL IPP-27: product of NOF CORPORATION), di-sec-butyl peroxydicarbonate (e.g. PEROYL SBP: product of NOF CORPORATION), t-butylperoxyisopropylcarbonate (e.g.KAYACARBON BIC-75: product of Kayaku Akzo Corporation) and bis(4-t-butylcyclohexyl)peroxydicarbonate (e.g. PEROYL TCP: product of NOF CORPORATION).

The addition amount of radical polymerization initiator depends on the curing temperature, the composition ratios of the radically polymerizable composition, the kinds, amounts and the like of the other additives to be blended in the composition and can not be flatly determined, however, it is generally preferable that the amount of radical polymerization initiator be 0.1 to 10 parts by mass, more preferably 1 to 5 parts by mass, most preferably 2 to 4 parts by mass based on 100 parts by mass of all the curable components in the radically polymerizable composition of the invention (IV) for plastic lens. If the amount of radical polymerization initiator is less than 0.1 parts by mass, curing of the composition might be insufficient, while if it exceeds 10 parts by mass, it is economically disadvantageous.

Next, the cured product of the invention (V) obtained by curing the radically polymerizable monomer of the invention (I) or the radically polymerizable polymer of the invention (II), or by curing a composition containing the radically polymerizable monomer of the invention (I) and/or the radically polymerizable polymer of the invention (II) is described.

In a case where the radically polymerizable composition of the invention is formed into plastic lens, cast molding is suitable for the formation process. As a specific example of the method, a method where, after adding radical polymerization initiator to the composition, the composition is injected through a line into a mold fixed with an elastomer gasket or a spacer and cured by heat in an oven can be cited.

In such a case, the material used for the mold is usually metal or glass. Generally, molds for forming plastic lens require washing after the cast-molding process, and as the detergent, strong alkali or strong acid is used. Glass, which is, unlike metal, not denatured by washing and can easily give a flat surface by polishing, is preferably used.

The curing temperature in forming the radically polymerizable composition of the invention (IV) into plastic lens depends on the composition ratio of the radically polymerizable composition and the kinds and amounts of the additives and cannot be flatly determined, however, generally it is about 20 to 150° C., preferably 30 to 120° C.

Moreover, in consideration for contraction and distortion caused by curing, it is preferable that the composition be gradually cured by raising the curing temperature. Generally, it is preferable that curing take 0.5 to 100 hours, preferably 3 to 50 hours, more preferably 10 to 30 hours.

The above plastic lens can be dyed in a similar manner with conventional lenses. Dyeing method is not particularly limited and any known dyeing method for plastic lens may be employed.

The radically polymerizable compound and radically polymerizable composition of the invention, having a high refractive index when cured, are particularly useful as optical materials for spectacles lens, camera lens, prism and the like.

EXAMPLES

Hereinafter, the invention will be more specifically described with reference to examples and comparative examples, but the invention is not limited thereto. The symbol "%" means "mass %" in the following Examples unless otherwise specified.

Measuring methods of the physical properties are described below.

1. Refractive Index (nD) and Abbe Number

A test piece of 9 mm×16 mm×4 mm was prepared and the refractive index (nD) and the Abbe number (vD) of the sample at 25° C. were measured with Abbe refractometer 1T, produced by ATAGO CO., LTD. As a contact liquid, α-bromonaphthalene was used.

2. $^1$H-NMR

Using model: JEOL EX-400(400 MHz)

The sample was dissolved in deuterated chloroform and measured using tetramethylsilane as a internal reference material.

3. FT-IR

Using model: Spectrum GX, product of Perkin Elmer Co., Ltd.

The sample was measured by ATR method.

4. GPC (Gel Permeation Chromatography)

Using Model:
Pump: DS-4, product of Showa Denko K.K.
Differential refractometer detector: RI-71, product of Showa Denko K.K.
Column used: Using by connecting three of K-801, K-802 and K-803 (all the columns are produced by Showa Denko K.K.)
Eluent: THF
Column temperature: 40° C.
Flow rate: 1 mL/min
Measuring method: Mn and Mw values were measured in terms of polystyrene.

5. Viscosity
The viscosity was measured by an E-type viscometer.
Apparatus used: TV-20 manufactured by TOKI SANGYO CO., LTD
Rotor used: 1°34'×24
Measurement temperature: 25° C.

6. Total Light Transmittance
The total light transmittance was measured according to JIS K7361-1.
Apparatus used: NDH2000 (manufactured by Nippon Denshoku Industries Co., Ltd.)
In the measurement, a flat plate having a thickness of 3 mm was used.

The following abbreviations are used in describing the Examples and Comparative Examples.
DAIP: diallyl isophthalate
DATP: diallyl terephthalate
VBz: vinyl benzoate
DADP: diallyl diphenate
DBM: dibenzyl maleate
ADC: diethyleneglycol bis(allylcarbonate)
(As ADC, RAV-7 AT ((product name): manufactured by Great Lakes Chemical Corporation) was used.)
BZMA: benzyl methacrylate
PEROCTA O:
1,1,3,3-tetramethylbutylperoxy-2-ethylhexanoate (Manufactured by Nof Corporation)
PERHEXA TMH:
1,1-di(t-hexylperoxy)-3,3,5-trimethylcyclohexane (Manufactured by Nof Corporation)

Example 1

To a round-bottomed flask equipped with a stirring bar, a dropping funnel and a thermometer, the compound (90 g) represented by formula (119) below,

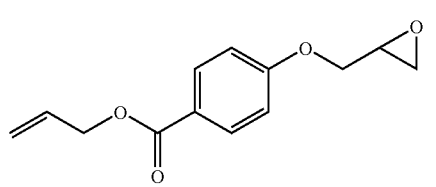
(119)

lithium bromide monohydrate (2 g) and tetrahydrofuran (200 mL) were charged and allowed to be under nitrogen atmosphere. Carbon disulfide (35.1 g) was charged to the dropping funnel and the temperature inside the flask was lowered to be about 10° C., followed hydropping the carbon disulfide to the reaction solution. When the dropping was finished, the reaction solution was adjusted to be room temperature and stirred for 5 hours. After the low-boiling compound was distilled away from the reaction solution under a reduced pressure with a evaporator, the obtained reactant was added ethyl acetate to separate from water. The organic layer was dried over anhydrous sodium sulfate and then the solvent was distilled off under a reduced pressure with a evaporator. The obtained solid was recrystallized from a mixed solution of ethyl acetate/hexane to obtain a pale yellow crystal (yield of 92 g).

It was identified that the product was a compound represented by the structural formula (120) below

Figure 2:
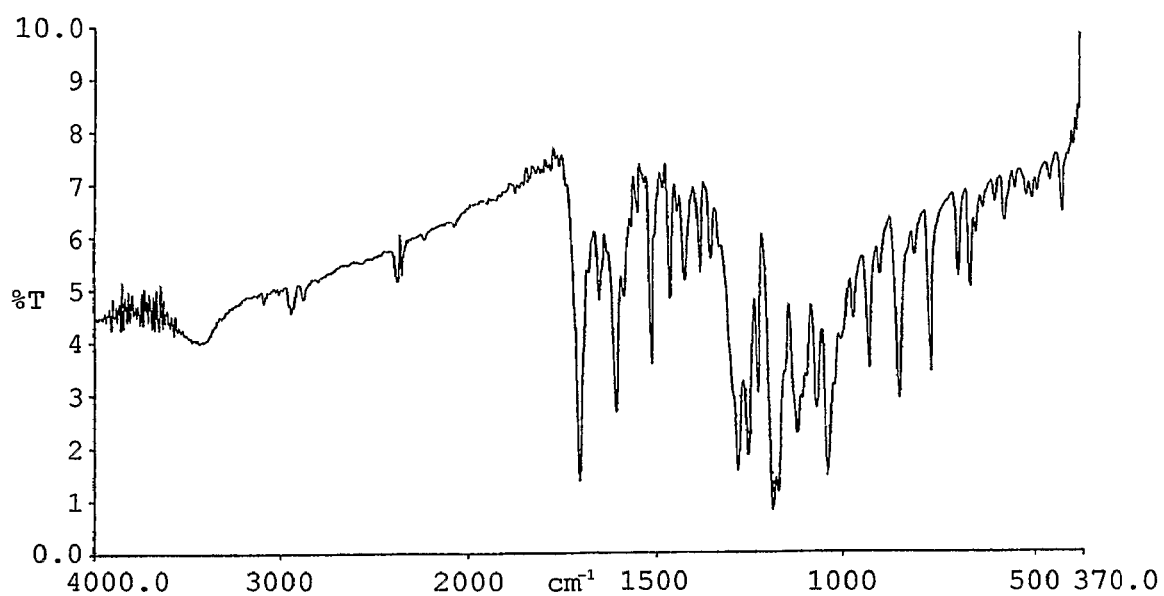
FIG. 2 shows a FT-IR spectrum of a radical polymerizable sulfur containing compound (Example 1) according to the invention.

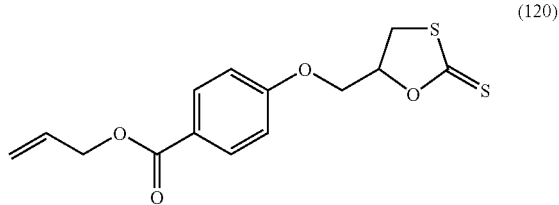
(120)

by $^1$H-NMR and FT-IR. The results of $^1$H-NMR and FT-IR measurements are shown in FIG. 1 and FIG. 2, respectively.

Example 2

After being replaced by nitrogen atmosphere, a 50 mL of schlenk equipped with a stirring bar was charged with the compound (50 g) obtained in Example 1, represented by the structural formula (120), and the compound was dissolved with chlorobenzene (15 mL). Next, to this was added methyl trifluoromethanesulfonate (36.5 μL) and the reaction solution was stirred for 7 hours at 60° C. After stirring, the reaction solution was cooled to room temperature. Methanol was added thereto and stirred for 30 minutes. Then, the reaction solution was added to 1 L of methanol to precipitate a polymer, which was subjected to vacuum-drying to obtain white polymer (3.29 g).

It was identified that the product was a polymer represented by the structural formula (121) below

Figure 3:
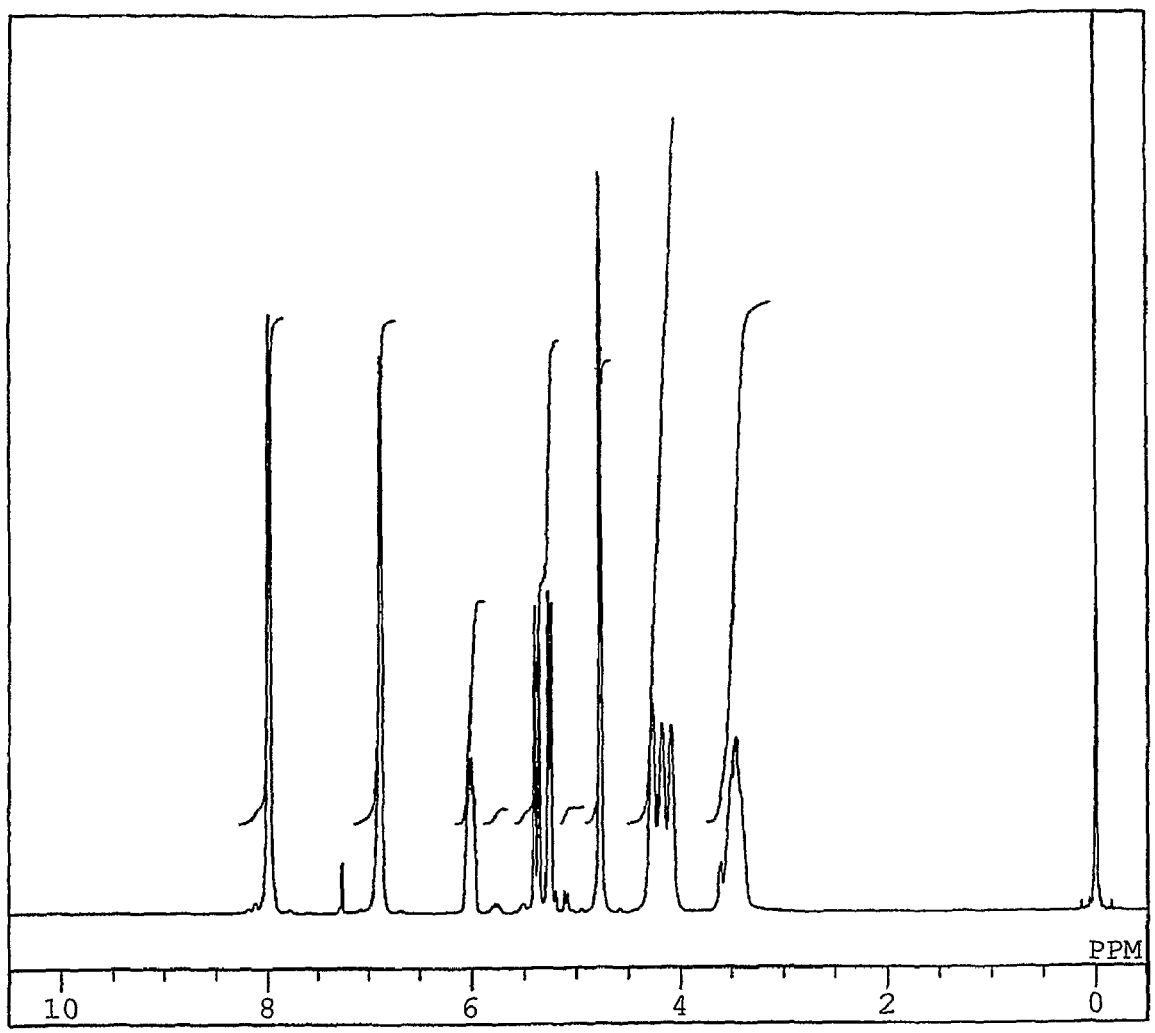
FIG. 3 shows a $^1$H-NMR spectrum of a radical polymerizable sulfur containing polymer (Example 2) according to the invention.
Figure 4:
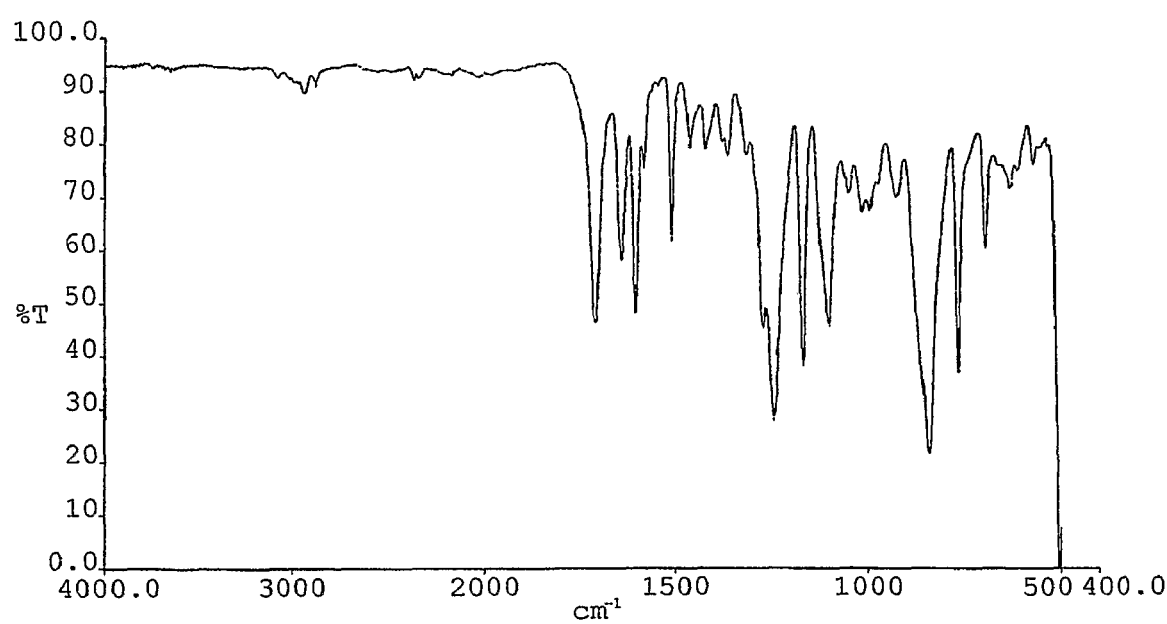
FIG. 4 shows a FT-IR spectrum of a radical polymerizable sulfur containing polymer (Example 2) according to the invention.

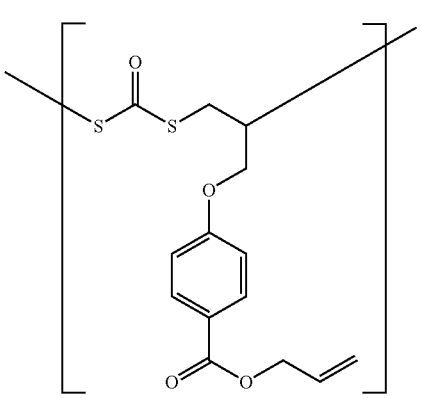
(121)

by $^1$H-NMR and FT-IR. The results of $^1$H-NMR and FT-IR measurements are shown in FIG. 3 and FIG. 4, respectively.

It was confirmed that the polymer had a number average molecular weight of 11400 and a weight average molecular weight of 13600 by GPC measurement.

The obtained white polymer (1.02 g) was dissolved in diallyl isophthalate (1.02 g), and to this was added perhexa TMH (0.04 g) (product of NOF CORPORATION) as a radical polymerization initiator followed by molding and curing. The molding and curing were conducted in a oven at 110° C. for 1 hour, at from 110 to 130° C. for 2 hours and at 130° C. for 1 hour sequentially as the temperature rising and heating were programmed. The obtained cured material had a refractive index of 1.600 and Abbe number of 30.1.

Example 3

To a 500 mL-volume flask equipped with a stirring bar and a thermometer after replaced by nitrogen atmosphere, the compound (50.0 g) represented by formula (120) obtained in Example 0.1 was added. Toluene (300 mL) was added thereto to thereby dissolve the compound. The temperature of the reaction solution was set to 60° C. and then methyl trifluoromethanesulfonate (2.1 g) was added thereto, followed by heating and stirring for 3.5 hours. After the heating and stirring, the reaction solution was cooled to room temperature and then methanol (0.84 g) was added thereto, followed by stirring.

To the reaction solution, silica gel (200 g) was added to prepare a slurry. After the solvent was removed from the slurry by using an evaporator and the reaction product was made supported by silica gel.

On the other hand, a column having a diameter of 8 cm was charged with silica gel in hexane slurry (500 g). At the top part of the column, the silica gel supporting the reaction product was placed. By using a developing solvent (ethyl acetate/hexane=1/4, volume ratio), components of low molecular weight were removed.

Next, the developing solvent was shifted to chloroform and polymer was eluted. When chloroform was removed from the chloroform solution containing polymer by using an evaporator, a white polymer (40 g) was obtained.

It was identified that the product was a polymer represented by the structural formula (121) by $^1$H-NMR and FT-IR.

It was confirmed that the polymer had a number average molecular weight of 4100 and a weight average molecular weight of 5100 by GPC measurement.

The obtained polymer was named as "polymer (A)".

Example 4

To a 500 mL-volume flask equipped with a stirring bar and a thermometer after replaced by nitrogen atmosphere, the compound (50.1 g) represented by formula (120) obtained in Example 1 was placed. Toluene (300 mL) was added thereto to thereby dissolve the compound. The temperature of the reaction solution was set to 60° C. and then methyl trifluoromethanesulfonate (4.22 g) was added thereto, followed by heating and stirring for 3.5 hours. After the heating and stirring, the reaction solution was cooled to room temperature and then methanol (1.65 g) was added thereto, followed by stirring.

To the reaction solution, silica gel (200 g) was added to prepare a slurry. After the solvent was removed from the slurry by using an evaporator and the reaction product was made supported by silica gel.

On the other hand, a column having a diameter of 8 cm was charged with silica gel in hexane slurry (500 g). At the top part of the column, the silica gel supporting the reaction product was placed. By using a developing solvent (ethyl acetate/hexane=1/4, volume ratio), components of low molecular weight were removed.

Next, the developing solvent was shifted to chloroform and polymer was eluted. When chloroform was removed from the chloroform solution containing polymer by using an evaporator, a white polymer (36.5 g) was obtained.

It was identified that the product was a polymer represented by the structural formula (121) by $^1$H-NMR and FT-IR.

It was confirmed that the polymer had a number average molecular weight of 2800 and a weight average molecular weight of 3400 by GPC measurement.

The obtained polymer was named as "polymer (B)".

Example 5

To a 100 mL-volume flask equipped with a stirring bar and a thermometer after replaced by nitrogen atmosphere, the compound (10.0 g) represented by formula (120) obtained in Example 1 was placed. Toluene (60 mL) was added thereto to thereby dissolve the compound. The temperature of the reaction solution was set to 60° C. and then methyl trifluoromethanesulfonate (0.42 g) was added thereto, followed by heating and stirring for 3.5 hours. After the heating and stirring, the reaction solution was cooled to room temperature and then methanol (0.166 g) was added thereto, followed by stirring.

To the reaction solution, silica gel (50 g) was added to prepare a slurry. After the solvent was removed from the slurry by using an evaporator and the reaction product was made supported by silica gel.

On the other hand, a column having a diameter of 6 cm was charged with silica gel in hexane slurry (100 g) At the top part of the column, the silica gel supporting the reaction product was placed. By using a developing solvent (ethyl acetate/hexane=1/4, volume ratio), components of low molecular weight were removed.

Next, the developing solvent was shifted to chloroform and polymer was eluted. When chloroform was removed from the chloroform solution containing polymer by using an evaporator, a white polymer (40 g) was obtained.

It was identified that the product was a compound represented by the structural formula (121) by $^1$H-NMR and FT-IR.

It was confirmed that the polymer had a number average molecular weight of 4200 and a weight average molecular weight of 5300 by GPC measurement.

The obtained polymer was named as "polymer (C)".

Example 6

Synthesis was conducted in reference to a document (Kihara, N.; Hara, N.; Endo, T. J. Org. Chem. 1995, 60, 473). That is, in a round-bottomed flask equipped with a stirring bar, a dropping funnel and a thermometer, phenylglycidylether (100 g), lithium bromide monohydrate (3.49 g) and tetrahydrofuran (200 mL) were placed and allowed to be under nitrogen atmosphere. Carbon disulfide (60.84 g) was placed in the dropping funnel and the temperature inside the flask was lowered to be about 10° C., followed by dropping the carbon disulfide to the reaction solution. When the dropping was completed, the temperature of the reaction solution was adjusted to be room temperature, followed by stirring for 5 hours. After components with low boiling points were distilled away from the reaction solution under a reduced pressure by using a evaporator, ethyl acetate was added to the obtained reaction product to separate from water layer. The organic layer was dried over anhydrous sodium sulfate and then the solvent was distilled off under a reduced pressure by using an evaporator. The obtained solid was recrystallized from toluene, to obtain a pale yellow crystal (yield of 78.9 g). It was identified that the product was a compound represented by the structural formula (122) below.

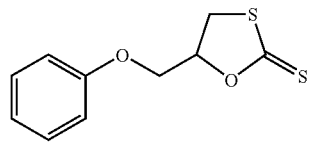

(122)

Example 7

Copolymerization

In a 100 mL-volume flask equipped with a stirring bar and a thermometer after replaced by nitrogen atmosphere, the compound (5 g) represented by formula (120) obtained in Example 1 and the compound (3.64 g) represented by formula (122) obtained in Example 6 were placed. Toluene (52 mL) was added thereto to thereby dissolve the compound. The temperature of the reaction solution was set to 60° C. and then methyl trifluoromethanesulfonate (435 mg) was added thereto, followed by heating and stirring for 4 hours. After the heating and stirring, the reaction solution was cooled to room temperature and then methanol (80 mg) was added thereto, followed by stirring.

To the reaction solution, silica gel (20 g) was added to prepare a slurry. After the solvent was removed from the slurry by using an evaporator and the reaction product was made supported by silica gel.

On the other hand, a column having a diameter of 8 cm was charged with silica gel in hexane slurry (200 g). At the top part of the column, the silica gel supporting the reaction product was placed. By using a developing solvent (ethyl acetate/hexane=1/4, volume ratio), components of low molecular weight were removed.

Next, the developing solvent was shifted to chloroform and polymer was eluted. When chloroform was removed from the chloroform solution containing polymer by using an evaporator, a white polymer (7.0 g) was obtained.

It was identified by $^1$H-NMR and FT-IR that the product was a polymer consisting of the structures 1 and 2 below.

Random polymer of structures 1 & 2

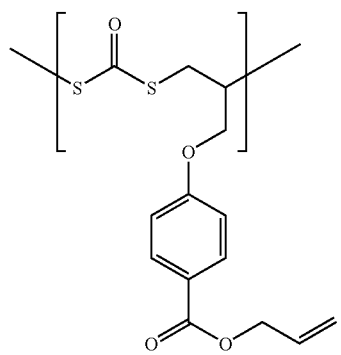

Structure 1

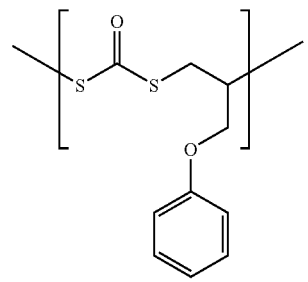

Structure 2

Figure 5:
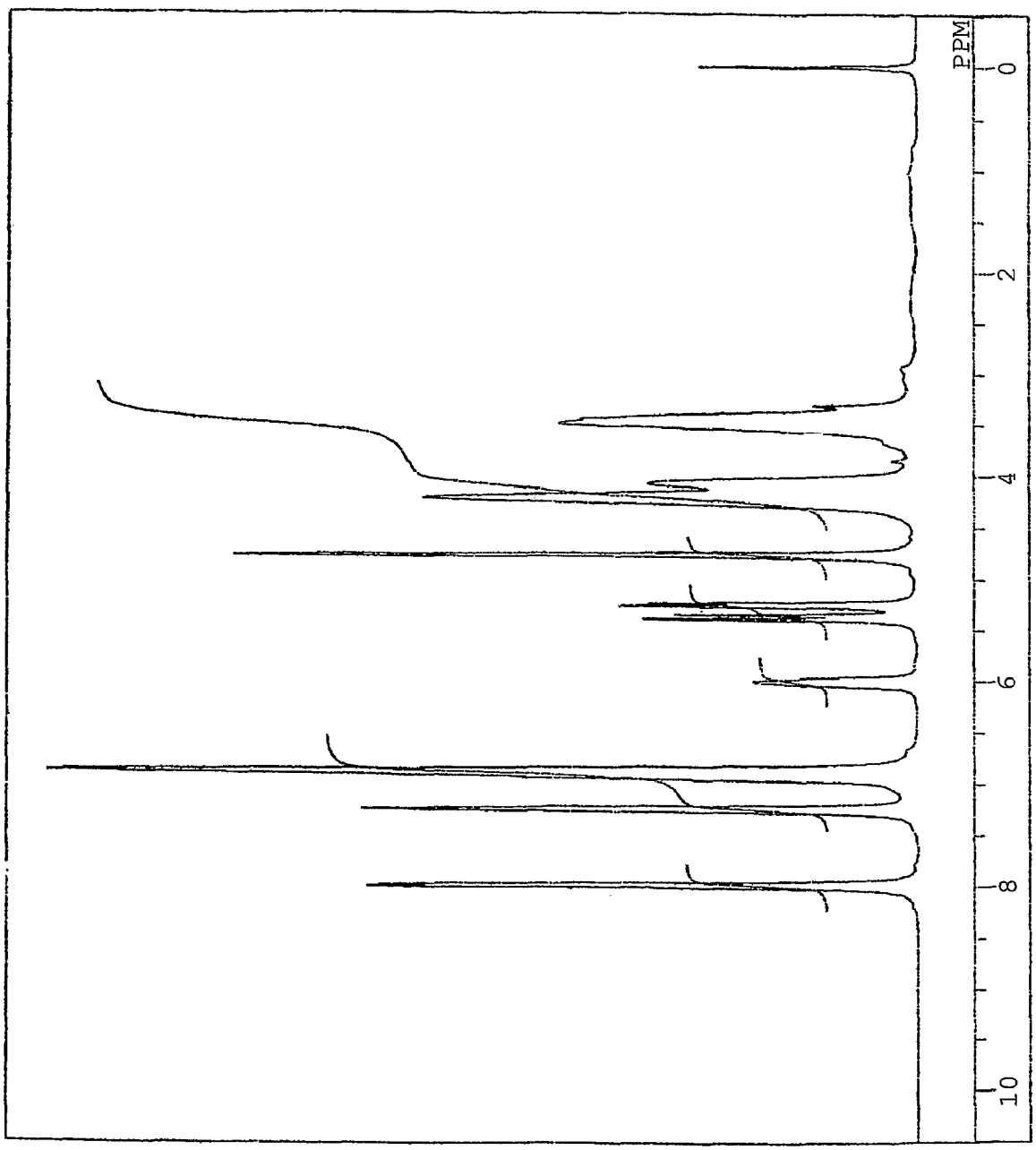
FIG. 5 shows a $^1$H-NMR spectrum of a radical polymerizable sulfur containing polymer (Example 7) according to the invention.
Figure 6:
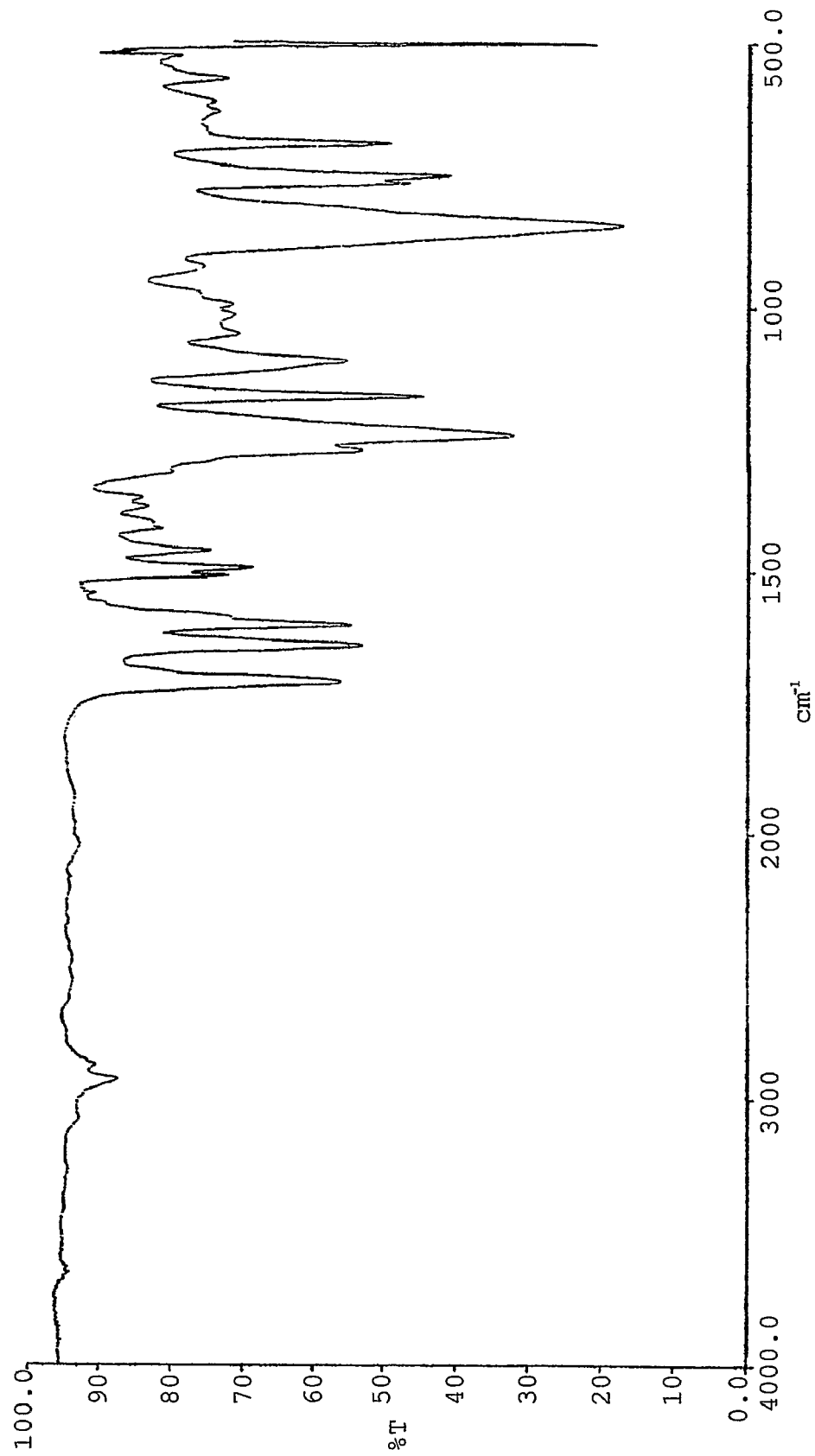
FIG. 6 shows a FT-IR spectrum of a radical polymerizable sulfur containing polymer (Example 7) according to the invention.

The results of $^1$H-NMR and FT-IR are shown in FIG. 5 and FIG. 6.

It was confirmed that the polymer had a number average molecular weight of 3400 and a weight average molecular weight of 4300 by GPC measurement.

The obtained polymer was named as "polymer (D)".

Comparative Example 1

Perhexa TMH (0.04 g) (product of NOF CORPORATION) as a radical polymerization initiator was added to diallyl isophthalate (2 g) followed by curing through cast-molding. The molding and curing were conducted in the same condition as in Example 2. The obtained cured material had a refractive index of 1.565 and Abbe number of 32.4.

Comparative Example 2

In a 1 L-volume three-necked flask equipped with a distillation apparatus, diallyl isophthalate (DAIP) (738.8 g, 3.0 mol), propylene glycol (76.1 g, 1.0 mol) and dibutyl tin oxide (0.739 g) were placed. The mixture was heated at 180° C. under nitrogen atmosphere and ally alcohol generated was removed. When about 81 g of allyl alcohol was removed, the inside of the reaction system was depressurized to 1.33 kPa to thereby increase the removal rate of allyl alcohol. After removing the theoretical amount (116.2 g) of allyl alcohol, heating was continued for another 1 hour. Subsequently, the inside of the reaction system was depressurized to 0.13 kPa and heating was further continued for another 1 hour. The reaction vessel was cooled to thereby obtain polymerizable composition (I) (699.0 g). When the polymerizable composition (I) was analyzed with gas chromatography, it was confirmed that the composition contained 43.6 mass % of DAIP.

It was identified by $^1$H-NMR that the product was a mixture of polymerizable oligomer represented by structural formula (124) and DAIP.

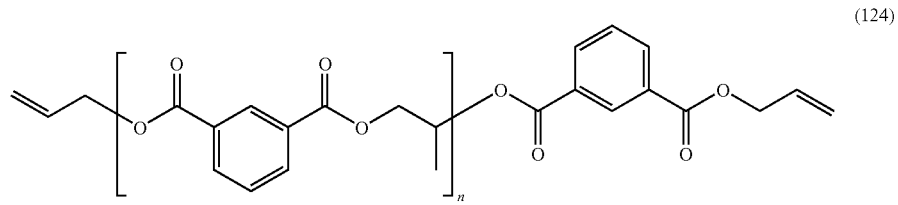

(124)

Examples 8 to 23 and Comparative Examples 3 to 5

By using polymers obtained in Examples 3 to 5 and 7 and polymerizable composition (I) obtained in Comparative Example 2, polymerizable compositions were prepared and the viscosity of each of the compositions was measured. To each of the polymerizable compositions, polymerization initiator was added in a predetermined amount and curing was conducted with a predetermined temperature program. The refractive index and the Abbe number of each of the cure products were measured. The blending ratio of the components of the compositions and the measurement results are shown in Tables 1 to 3.

Since polymerizable composition (I) obtained in Comparative Example 2 contained 43.6 mass % of diallyl isophthalate (DAIP), in preparation of the polymerizable compositions shown in Table 3, DAIP was further added to polymerizable composition (I).

TABLE 1

| | Example No. | | | | | | | | | |
|---|---|---|---|---|---|---|---|---|---|---|
| | 2 | 8 | 9 | 10 | 11 | 12 | 13 | 14 | 15 | 16 |
| Polymer used | Example 2 | Example 3 Polymer (A) | Example 3 Polymer (A) | Example 3 Polymer (A) | Example 3 Polymer (A) | Example 3 Polymer (A) | Example 3 Polymer (A) | Example 3 Polymer (A) | Example 3 Polymer (A) | Example 3 Polymer (A) |
| Mn | 11400 | 4100 | 4100 | 4100 | 4100 | 4100 | 4100 | 4100 | 4100 | 4100 |
| Mw | 13600 | 5100 | 5100 | 5100 | 5100 | 5100 | 5100 | 5100 | 5100 | 5100 |
| Polymer (%) | 50 | 30 | 10 | 49 | 50 | 45 | 45 | 49 | 48 | 48 |
| DAIP (%) | 50 | 70 | 90 | 22 | 12 | 20 | 20 | 21 | 20 | 16 |
| DATP (%) | — | — | — | — | — | — | — | — | — | — |
| ADC (%) | — | — | — | 3 | 3 | — | — | — | — | — |
| DBM (%) | — | — | — | — | — | 10 | 5 | — | — | 6 |
| DADP (%) | — | — | — | 6 | 5 | 5 | 5 | — | 2 | — |
| BzMA (%) | — | — | — | 20 | 30 | — | — | — | — | — |
| VBz (%) | — | — | — | — | — | 20 | 25 | 30 | 30 | 30 |
| Viscosity before Curing(mPa · S) | | 227 | 26 | 1220 | 762 | 600 | 442 | 428 | 397 | 449 |
| Initiator | TMH | TMH | TMH | TMH | TMH | TMH | TMH | OO | OO | OO |
| Initiator amount(phr) | 2 | 4 | 4 | 4 | 4 | 4 | 4 | 2 | 2 | 2 |
| Temperature program for curing* | (I) | (I) | (I) | (I) | (I) | (I) | (I) | (II) | (II) | (II) |
| Refractive index of cured product | 1.6000 | 1.5856 | 1.5737 | 1.5984 | 1.5933 | 1.6000 | 1.5999 | 1.6004 | 1.6005 | 1.5998 |
| Abbe number of cured product | 30.1 | 29.0 | 30.4 | 29.7 | 30.2 | 27.9 | 29.9 | 27.4 | 27.9 | 28.5 |

TABLE 2

| | Example No. | | | | | | |
|---|---|---|---|---|---|---|---|
| | 17 | 18 | 19 | 20 | 21 | 22 | 23 |
| Polymer used | Example 4 Polymer (B) | Example 4 Polymer (B) | Example 4 Polymer (B) | Example 5 Polymer (C) | Example 5 Polymer (C) | Example 5 Polymer (C) | Example 7 Polymer (D) |
| Mn | 2800 | 2800 | 2800 | 4200 | 4200 | 4200 | 3400 |
| Mw | 3400 | 3400 | 3400 | 5800 | 5800 | 5800 | 4300 |
| Polymer (%) | 40 | 50 | 60 | 50.2 | 49.1 | 49 | 30 |
| DAIP (%) | — | — | — | — | — | — | 70 |
| DATP (%) | 30 | 20 | 10 | 20 | 18.6 | 21 | — |
| ADC (%) | — | — | — | — | — | — | — |
| DBM (%) | — | — | — | — | — | 4.8 | — |
| DADP (%) | — | — | — | — | 2.4 | — | — |

TABLE 2-continued

| | Example No. | | | | | | |
|---|---|---|---|---|---|---|---|
| | 17 | 18 | 19 | 20 | 21 | 22 | 23 |
| BzMA (%) | — | — | — | — | — | — | — |
| VBz (%) | 30 | 30 | 30 | 29.8 | 29.9 | 25.2 | — |
| Viscosity before Curing (mPa · S) | 101 | 311 | 1052 | 540 | 491 | 632 | 220 |
| Initiator | OO | OO | OO | OO | OO | OO | TMH |
| Initiator amount (phr) | 2.4 | 2.8 | 2.5 | 2.4 | 2.8 | 2.4 | 4 |
| Temperature program for curing* | (II) | (II) | (II) | (II) | (II) | (II) | (I) |
| Refractive index of cured product | 1.5936 | 1.5984 | 1.6070 | 1.6020 | 1.5990 | 1.6000 | 1.5900 |
| Abbe number of cured product | 30.6 | 29.2 | 30.0 | 29.0 | 28.0 | 29.0 | 30.0 |

TABLE 3

| | Comparative Example No. | | | |
|---|---|---|---|---|
| | 1 | 3 | 4 | 5 |
| | | The polymerizable composition (I) obtained in Comparative Example 2 was used DAIP: 43.6% Polymerizable oligomer: 56.4% | | |
| Polymerizable oligomer | — | 30 | 10 | — |
| DAIP (%) | 100 | 70 | 90 | — |
| DATP (%) | — | — | — | — |
| ADC (%) | — | — | — | 100 |
| DBM (%) | — | — | — | — |
| DADP (%) | — | — | — | — |
| BzMA (%) | — | — | — | — |
| VBz (%) | — | — | — | — |
| Initiator* | TMH | TMH | TMH | TMH |
| Initiator amount (phr) | 4 | 4 | 4 | 4 |
| Temperature program for curing* | (I) | (I) | (I) | (I) |
| Refractive index of cured product | 1.5650 | 1.5672 | 1.5695 | 1.5000 |
| Abbe number of cured product | 32.4 | 34.0 | 35.0 | 58.0 |

*Polymerization initiator
TMH: PERHEXA TMH
OO: PEROCTA O
**Temperature programs for curing
(I): 110° C.→ (1 h) → 110° C.→ (2 h) → 130° C.→ (1 h) → 130° C.
(II): 50° C. → (2 h) → 50° C. → (3 h) → 60° C. → (14 h) → 80° C. → (3 h) → 90° C. → (2 h) → 90° C.

Example 24

A composition consisting of the polymer obtained in Example 3 (45 mass %), diallyl terephthalate (DATP) (20 mass %), vinylbenzoate (VBz) (25 mass %) anddibenzylmaleate (DBM) (5 mass %) was prepared. To the composition, 1,1,3,3-tetramethylbutylperoxy-2-ethylhexanoate (PEROCTA O manufactured by NOF CORPORATION) (2 mass parts based on 100 mass parts of the composition) was added as a radical polymerization initiator and defoaming was conducted under reduced pressure.

The obtained composition was poured into a lens mold consisting of glass-mold and a gasket. Then, the lens mold was placed in an oven for heating at 50° C. for 2 hours. Subsequently, the temperature was increased from 50° C. to 60° C. over 3 hours. The temperature was further increased from 60° C. to 80° C. over 14 hours, and furthermore the temperature was increased from 80° C. to 90° C. over 3 hours. Then, heating was continued at 90° C. for another 2 hours. After the temperature was gradually cooled to room temperature, the cured product was taken out of the lens mold and subjected to annealing treatment by heating at 120° C. for 2 hours in an oven.

The obtained cured product was colorless and transparent and no optical distortion was observed. The refractive index was 1.600, the Abbe number was 30, and the total light transmittance was 90%.

INDUSTRIAL APPLICABILITY

By using the radically polymerizable sulfur-containing compound of the invention (I) and/or the radically polymerizable sulfur-containing polymer of the invention (II), the novel radically polymerizable composition of the invention (IV) and the cured product of the invention (V) can be obtained. The cured product obtained by curing the invention (I), (II), (III) or (IV), which has a high refractive index, is especially useful as an optical material.

The invention claimed is:

1. A radically polymerizable sulfur-containing compound comprising a group represented by formula (1)

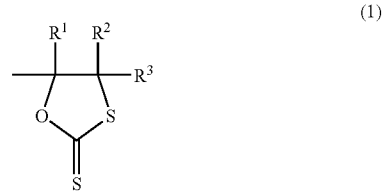

(1)

wherein $R^1$ to $R^3$ each independently represents a hydrogen atom or an alkyl group having 1 to 4 carbon atoms, and at least one selected from among groups represented by formulae (2) to (4)

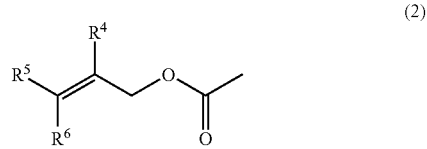

(2)

-continued

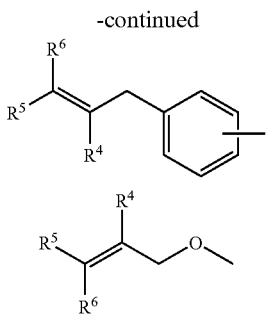
(3)

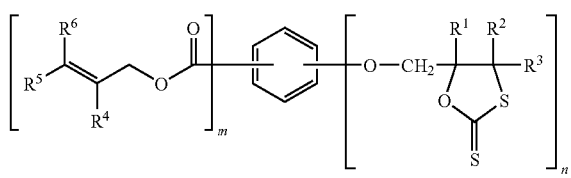
(4)

wherein $R^4$ to $R^6$ each independently represents a hydrogen atom or an alkyl group having 1 to 4 carbon atoms.

2. The radically polymerizable sulfur-containing compound as claimed in claim 1, which is represented by formula (5)

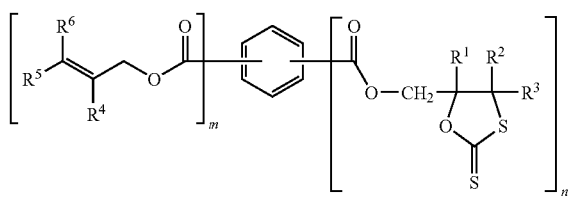
(5)

wherein $R^1$ to $R^6$ each independently represents a hydrogen atom or an alkyl group having 1 to 4 carbon atoms, and m and n each independently represents an integer of 1 to 5, with a proviso that $m+n \leqq 6$.

3. The radically polymerizable sulfur-containing compound as claimed in claim 1, which is represented by formula (6)

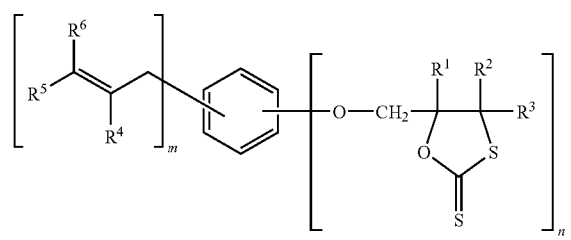
(6)

wherein $R^1$ to $R^6$ each independently represents a hydrogen atom or an alkyl group having 1 to 4 carbon atoms, and m and n each independently represents an integer of 1 to 5, with a proviso that $m+n \leqq 6$.

4. The radically polymerizable sulfur-containing compound as claimed in claim 1, which is represented by formula (7)

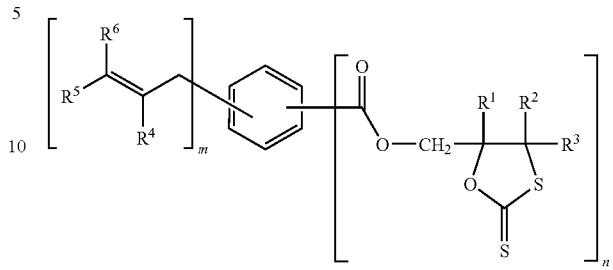
(7)

wherein $R^1$ to $R^6$ each independently represents a hydrogen atom or an alkyl group having 1 to 4 carbon atoms, and m and n each independently represents an integer of 1 to 5, with a proviso that $m+n \leqq 6$.

5. The radically polymerizable sulfur-containing compound as claimed in claim 1, which is represented by formula (8)

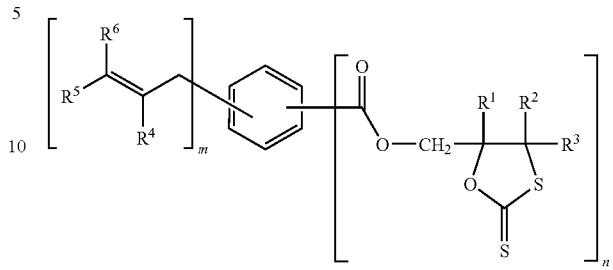
(8)

wherein $R^1$ to $R^6$ each independently represents a hydrogen atom or an alkyl group having 1 to 4 carbon atoms, and m and n each independently represent an integer of 1 to 5, with a proviso that $m+n \leqq 6$.

6. The radically polymerizable sulfur-containing compound as claimed in claim 1, which is represented by formula (9)

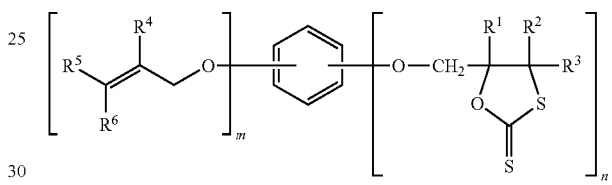
(9)

wherein $R^1$ to $R^6$ each independently represents a hydrogen atom or an alkyl group having 1 to 4 carbon atoms, and m and n each independently represents an integer of 1 to 5, with a proviso that $m+n \leqq 6$.

7. The radically polymerizable sulfur-containing compound as claimed in claim 1, which is represented by formula (10)

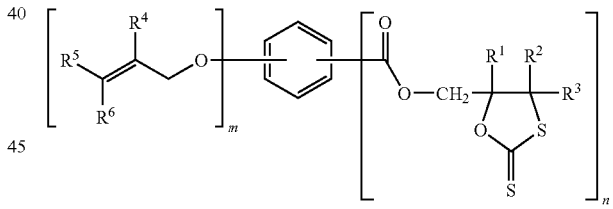
(10)

wherein $R^1$ to $R^6$ each independently represents a hydrogen atom or an alkyl group having 1 to 4 carbon atoms, and m and n each independently represents an integer of 1 to 5, with a proviso that $m+n \leqq 6$.

8. The radically polymerizable sulfur-containing compound as claimed in claim 2 wherein m is 1 and n is 1.

9. The radically polymerizable sulfur-containing compound as claimed in claim 1, wherein all of $R^1$ to $R^6$ are hydrogen atoms.

10. The radically polymerizable sulfur-containing compound as claimed in claim 1, which is in the form of an optical material.

11. A method for producing a radically polymerizable sulfur-containing polymer, wherein the radically polymerizable sulfur-containing compound described in claim 1 is subjected to cationic ring-opening polymerization in the presence of a catalyst.

12. A method for producing a radically polymerizable sulfur-containing polymer, wherein at least one compound described in claim 1 and another different compound having a group represented by formula (1) are subjected to cationic ring-opening copolymerization in the presence of a catalyst

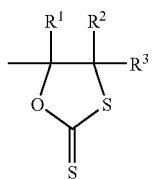

(1)

wherein $R^1$ to $R^3$ have the same meanings as defined in claim 1.

13. The method for producing a radically polymerizable sulfur-containing polymer as claimed in claim 11, wherein the catalyst is at least one selected from the group consisting of methyl trifluoromethane sulfoniate, ethyl trifluoromethane sulfonate and trifluoroboron-diethylether adduct.

\* \* \* \* \*